United States Patent
Galstian et al.

(10) Patent No.: US 10,285,803 B2
(45) Date of Patent: May 14, 2019

(54) INDUCTIVE COIL SENSOR FOR VISION CORRECTIVE APPARATUS AND METHODS THEREFOR

(71) Applicant: LENSVECTOR INC., Sunnyvale, CA (US)

(72) Inventors: Tigran Galstian, Quebec (CA); Denis Brousseau, St-Jean-Chrysostome (CA)

(73) Assignee: LENSVECTOR INC., Sunnyvale, CA (US)

( * ) Notice: Subject to any disclaimer, the term of this patent is extended or adjusted under 35 U.S.C. 154(b) by 277 days.

(21) Appl. No.: 14/956,145

(22) Filed: Dec. 1, 2015

(65) Prior Publication Data

US 2016/0081793 A1  Mar. 24, 2016

Related U.S. Application Data

(63) Continuation of application No. PCT/CA2014/050532, filed on Jun. 9, 2014.

(60) Provisional application No. 61/832,728, filed on Jun. 7, 2013.

(51) Int. Cl.
| | |
|---|---|
| *G02C 7/00* | (2006.01) |
| *G02C 7/02* | (2006.01) |
| *G02C 7/04* | (2006.01) |
| *A61F 2/16* | (2006.01) |
| *G02C 7/08* | (2006.01) |

(52) U.S. Cl.
CPC .......... *A61F 2/1624* (2013.01); *A61F 2/1635* (2013.01); *G02C 7/04* (2013.01); *G02C 7/081* (2013.01); *G02C 7/083* (2013.01); *A61F 2250/0002* (2013.01)

(58) Field of Classification Search
CPC ........ A61F 2/1624; A61F 2/1613; A61F 2/14; A61F 2250/0001
USPC ............................ 351/159.03; 623/6.22–6.24
See application file for complete search history.

(56) References Cited

U.S. PATENT DOCUMENTS

| | | |
|---|---|---|
| 2012/0140167 A1 | 6/2012 | Blum |
| 2013/0218270 A1 | 8/2013 | Blanckaert et al. |

FOREIGN PATENT DOCUMENTS

WO    WO 2012/006691 A1    1/2012

OTHER PUBLICATIONS

Babic et al., Mutual Inductance Calculation between Circular Coils with Lateral and Angular Misalignment, PIERS Proceedings, Moscow, Russia, Aug. 18-21, 2009.
PCT/CA2014/050532 IPRP dated May 5, 2015.
PCT/CA2014/050532 ISR with related claims.
(Continued)

*Primary Examiner* — Mahidere S Sahle
(74) *Attorney, Agent, or Firm* — Arent Fox LLP

(57) ABSTRACT

An ocular adaptive lens prosthesis apparatus is provided. In some implementations the apparatus includes a tunable liquid crystal lens encapsulated in the ocular prosthesis with control electronics and a power source. The tunable liquid crystal lens is driven in response to a convergence signal to provide accommodation. In some embodiments the tunable liquid crystal device corrects other visual shortcomings of the natural eye. The ocular prosthesis has a remote programmable tunable liquid crystal lens controller configured to recalibrate the tunable liquid crystal lens to compensate for dynamic adaptation of the eye over time. A coil is employed to transmit a convergence signal between a pair of ocular prostheses in a dual eye vision correction system.

23 Claims, 25 Drawing Sheets

(56) References Cited

OTHER PUBLICATIONS

PCT/CA2014/050532 Search Strategy.
PCT/CA2014/050532 Written Opinion.
Syrpailyne et al., A Novel Magnetic Stimulator Using Parallel Excited Coils and Capable of High Frequency Stimulation, Journal of Medical Devices. Mar. 2014; 8(1-9).
Vdovin, G. et al., On the Possibility of Intraocular Adaptive Optics. Opt Express. Apr. 7, 2003; 11(7):810-7.

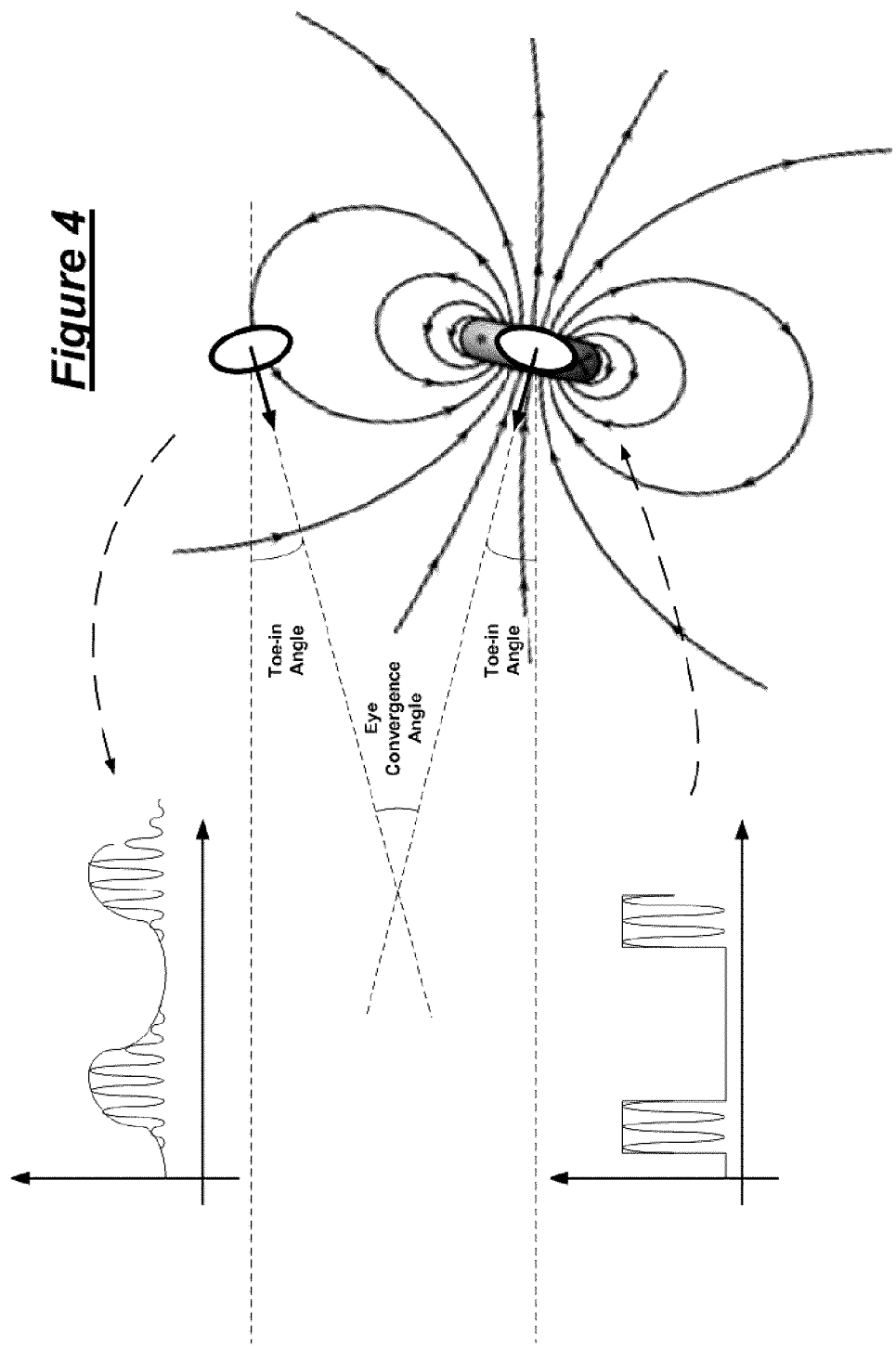

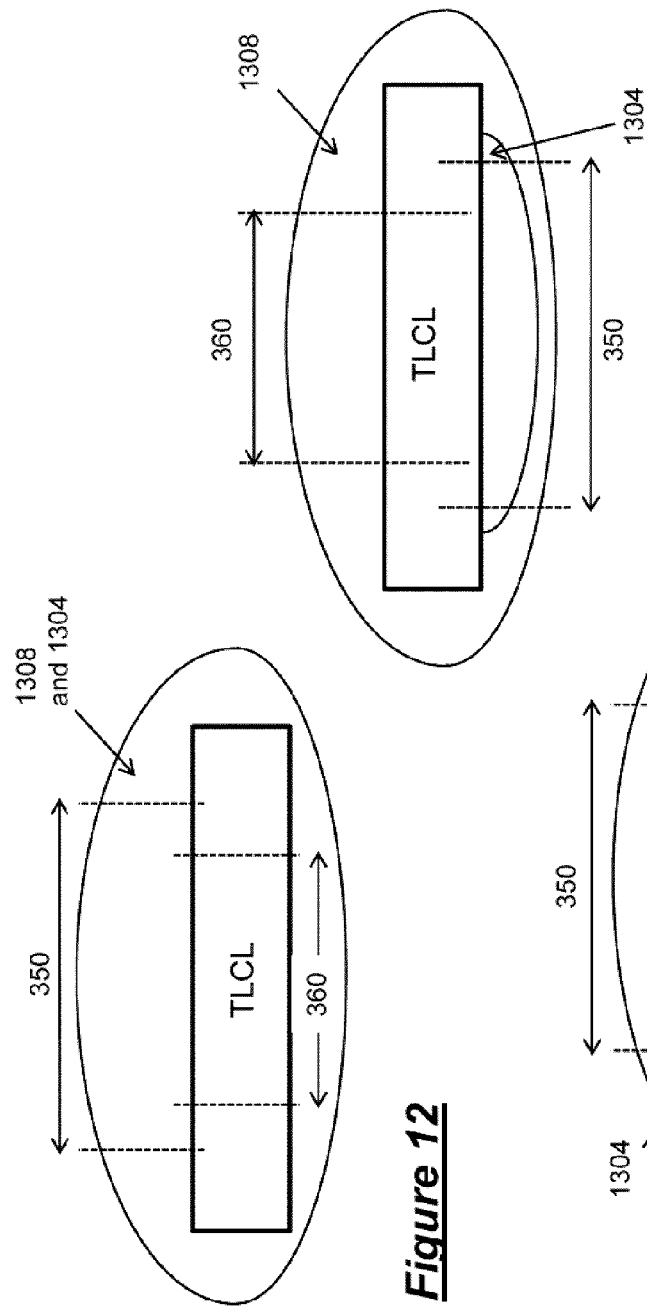

INDUCTIVE COIL SENSOR FOR VISION CORRECTIVE APPARATUS AND METHODS THEREFOR

This application claims priority to International Application No. PCT/CA2014/050532, filed Jun. 9, 2014 which claims priority of U.S. patent application Ser. No. 61/832,728 filed on Jun. 7, 2013, the entirety of each of which is hereby incorporated by reference.

TECHNICAL FIELD

This invention relates to an electromagnetic sensor for vision correction devices, and in particular to contact lenses and intra-ocular lens implants which use an inductive coil in the control of vision correction devices, as well as related apparatus and methods.

BACKGROUND

Various conditions are addressed by fitting an eye with an intraocular lens to replace a natural crystalline lens of the eye. As well, contact lenses can be employed in correcting vision.

The human eye is known to naturally evolve in time. This evolution may change the geometry of the eye optics, the dynamics of its operation, its transmittance and accommodative capacity. Age related eye changes are described for example in "Age-Related Changes of the Human Eye" by Carlo A. P. Cavallotti, Luciano Cerulli, 2008, Springer. Changes in the geometry of the eye optics may be also be provoked by various interventions, such as eye surgery or a LASIK (Laser-Assisted in situ Keratomileusis) operation.

For example, development of a cataract (the decrease of eye's light transmission) is a common condition experienced with age. To improve light transmission, the eye is typically fitted with a plastic IntraOcular Lens (IOL) during cataract surgery, a well know medical procedure. Such an IOL may also be designed to adjust the total optical power of the eye. A goal of cataract surgery has long been to provide, post-operatively, unaided (without wearing glasses, including progressive ones) clear and high-quality distance, intermediate and near vision. However, such results are hard to attain. The current solutions do not enable dynamic distance accommodation capacity (controlled focus range); in fact cataract surgery may even degrade distance accommodation capacity:

Basic attempts to restore vision have included surgically empting a capsular bag, in which the natural crystalline lens of the eye resides, and refilling it with an accommodating polymer intended to match the behavior of a juvenile lens. While such attempts have received considerable attention, an effective actualization remains elusive today in part because properties of homogeneous polymers are insufficient to mimic properties of an inhomogeneous natural crystalline lens. In an article entitled "Accommodating IOLs: Emerging Concepts and Designs" published July 2004 in Cataract & Refractive Surgery Today, Samuel Masket MD describes difficulties in characterizing a crystalline lens in situ, which is subject to forces exerted by adjoining tissues, attesting to an inability to create an implant having desired properties under forces exerted by adjoining tissues postoperatively. Postoperative changes in adjoining tissues vary with the nature of the implant material and its contact with an anterior capsule of the eye. As well, any crystalline lens characterization is necessarily performed on an imperfect lens slated for invasive medical removal with the desire of providing a perfect intraocular prosthesis aided vision postoperatively. Even if a characterization of the crystalline lens from an earlier age would have been available, the surrounding tissues heal unevenly and also change with age rendering such characterization insufficient overall.

Implanting a fixed focus (monofocal) lens has been attempted in the prior art with a limited degree of success. Postoperatively, the combination of the remaining adjoining tissues and fixed focus lens provide only a limited degree of accommodation, compared to the juvenile natural lens, between 0.5 to 1.5 diopter pseudoaccommodation. In comparison, research by Mitchell Scheiman and Bruce Wick in "Clinical Management of Binocular Vision", Lippincott, New York, 1994 suggests that on average a juvenile lens provides 18 diopters variability in average amplitude of accommodation. Generally, the average amplitude of accommodation at a given age may be estimated by Hofstetter's formula: 18.5 minus one third of the patient's age in years. Therefore, while a monofocal intraocular implant may provide clearer vision post operatively, the limited degree of post operative accommodation requires additional visual aids such as glasses or contact lenses. Dual optic prostheses have been implanted however suffer from low optical power variability in the range of 2.5 diopters.

Another example of a medical condition experienced by the majority of people with age is presbyopia (the loss of distance accommodation capacity). With age sufferers develop a flat eye lens, which is well adapted for distant vision, but not for mid or near distance vision.

Various flexible plastic monofocal lens systems were proposed, which rely on the mechanical deformation or a shift (such as Crystalens by Bausch & Lomb) induced by the muscular (such as ciliary) activity to provide variable optical power for dynamic distance accommodation. However, the ciliary muscle is a very complex organ (Johannes W. Rohen, "Scanning Electron Microscopic Studies of the Zonular Apparatus in Human and Monkey Eyes", 1979 Assoc. for Res. In Vis. And Ophthal., inc., pp. 133-143), which constantly evolves with age and which is regarded too unreliable to propose solutions depending on it.

A further proposal includes multifocal IOLs, which have a diffractive structure and able to focus simultaneously far, mid and near distance objects on the retina. This however requires the brain to learn to select the appropriate zones. Multifocal IOLs may also produce visual side effects for distance vision and night vision; problems including glare, halos and the like.

Alternatively, electrically driven liquid lenses (U.S. Pat. No. 4,816,031; US 2007/0100443 A1) and liquid-crystal lenses (Elenza, U.S. Pat. No. 7,926,940; U.S. 61/441,863; "On the Possibility of Intraocular Adaptive Optics", G. Vdovin et al., 7 Apr. 2003/Vol. 11, No. 7/OPTICS EXPRESS 810; "Liquid-Crystal Intraocular Adaptive Lens with Wireless Control", A. N. Simonov et al., 11 Jun. 2007/Vol. 15, No. 12/OPTICS EXPRESS 7468) have been proposed as accommodative or Electrical IOLs (EIOLs). The optical power of such lenses may be changed gradually (by means of a tunable refractive lens) or in a discrete manner (by means of a tunable diffractive lens), see for example 14.5 L: Late-News Paper: "Comparisons Between a Liquid Crystal Refractive Lens and a Diffractive Lens for 3D Displays", L. Lu et al., ISSN 0097-966X/11/4201-0171-$1.00 © 2011 SID, with the help of an electrical signal controlled by an Application Specific Integrated Circuit (ASIC) driver powered by a miniature remote chargeable battery.

Namely, tunable liquid crystal lenses have been proposed for use in active accommodation for example:

Tunable Liquid Crystal (TLC) optical devices are described, for example in International Patent Application publications WO/2007/098602 and WO/2009/153764. TLC optical devices are flat multi-layered structures having a Liquid Crystal (LC) layer. Good optical lens power can be achieved within a relatively small thickness. The liquid crystal layer has a (non-uniform) spatially modulated refractive index which changes in response to a spatially modulated electric field applied thereto. Moreover, liquid crystal refractive index variability is responsive to a time variable electric field. The principle of operation of the TLC optical device is the attenuation of the electrical potential, and the corresponding drop in electric field strength across an optical aperture between the periphery and the center of the TLC optical device. With an appropriate geometry, a variety of optical components employing TLC optical devices can be built, for example: a tunable lens, a corrective optical element, iris, etc. Tunable Liquid Crystal Lenses (TLCLs) provide significant advantages being thin and compact. The performance of TLCLs may be measured by a multitude of parameters, including: a tunable focus range, optical power (diopter) range, power consumption, transmittance, etc.

SUMMARY

Whether for an intraocular implant or a contact lens having a tunable liquid crystal lens driven in response to an electrical drive signal to provide focus control, the ocular prosthesis controller must somehow obtain information about the patient's desired optical power or accommodation distance to be able to generate the appropriate electrical drive signal for the eIOL's adaptation to change optical power to an appropriate value.

On providing a trigger for accommodation, several physiological mechanisms might be used as source for information such as desired optical power or accommodation distance. It is known that neural signaling, requesting accommodation, propagates as electrical pulses and induces changes in ion concentration (US 2010/0004741 A1). The degree of ciliary muscle contraction is then changed, followed by a change in the crystalline lens' shape and its optical power. At the same time, the pupil diameter is changed and the vergence (angular convergence) of the two eyes is modified. These physiological variations might be used as sensing mechanisms to generate the required signal for the electrical accommodation control.

Electric and electromagnetic sensors can be used to detect electrical activity in the vicinity of the ciliary muscle. This can be, among others, the electrical signal generated due to muscular activity, which can be detected by electromyography techniques detecting the electrical potential generated by muscle cells when the cells are electrically or neurologically activated.

Because the human eye is a very complex dynamic system, continuously changing its parameters and its environment, ion concentration changes would be rather complicated to detect and particularly complicated to relate unambiguously to the desired degree of accommodation. For the same reasons, the use of pressure, stress or deformation detection would be very difficult since such variations must be detected by corresponding sensors, which must be installed in a complex and evolving environment such as the ciliary muscle. In addition, mechanical forces in the eye are subject to change noticeably with age (M. T. Pardue et al., "Age-Related Changes in Human Ciliary Muscle", Optometry and Vision Science, V. 77, No. 4, April 2000, pp. 204-210; and S. A. Strenk et al., "Age-Related Changes in Human Ciliary Muscle and Lens: A Magnetic Resonance Imaging Study", Investigative Ophthalmology & Visual Science, May 1999, v. 40, No. 6, Copyright: Association for research in Vision and Ophthalmology). Therefore such mechanisms are not very reliable for triggering desired accommodation and errors in the electrical signal representing the degree of desired accommodation remain difficult to overcome.

As well, it is well known that the pupil diameter may change not only for distance accommodation but also for light intensity variation. Therefore pupil constriction/dilation cannot be relied upon (exclusively) as a triggering signal for distance accommodation because of the ambiguity in pupil diameter changes.

The degree of alignment of the eyes is a source of information not explored in the prior art (FIG. 3A), namely as the two eyes align more or less parallel when the person looks at a distant object and converge as the distance to the observed object diminishes. Thus, one may employ microscopic gyroscopes in each eye to detect eye alignment and use wireless communication between gyroscope controllers 'interrogating' them to generate the accommodation signal. However, eye alignment is also a very complex phenomenon and may change for various reasons. For example, the eyes employ synchronized quick angular movements known as saccades (simultaneous movements of both eyes in the same direction), while they are not necessarily synchronized in their angular movements employing small angular drifts having amplitudes between 2 to 120 arcmin known as microsaccades motion.

The use of an inductive coil was suggested in the prior art for external signal reception (Vdovin et al. mentioned herein above).

Two inductive coils can be mutually coupled if they are driven by an AC signal (FIG. 4). For reception (detection and processing), the degree of the mutual coupling of the two coils can change depending upon their distance, relative angular orientation in the horizontal plane and the electromagnetic properties of the surrounding media.

In accordance with one aspect of the proposed solution, there is provided a system for sensing and for electrical signal generation based on employing mutually inductive coupled electromagnetic coil detectors. The specific signal processing provided by a dynamic remotely reprogrammable and/or self-trainable (adaptive) algorithm identifies the desired degree of accommodation to provide a vision corrective optical system having a pair of integral cooperative (implantable/contact lens) ocular prostheses for consorted dynamic adaptation.

In accordance with another aspect of the proposed solution an integral (implantable) opto-electronic device is proposed which includes an electromagnetic mutually coupled inductive coil sensing system enabled for dynamic reprogramming (training) of its processing unit.

In some embodiments of the proposed solution, each of a pair of tunable liquid crystal lens (or any other suitable tunable lens) ocular prostheses (contact lenses or implants) includes an inductive coil, each inductive coil is configured to participate as an inductor in a resonant circuit (when power is transmitted thereto), each inductive coil being configured to controllably generate a varying magnetic field detectable by the other inductive coil, each inductive coil being configured to detect the varying magnetic field of the other inductive coil. A focusing distance is determined from a degree of toe-in derived from detected variances of the magnetic fields and a preset eye-to-eye distance.

In accordance with a further aspect of the proposed solution, a pair of electronic circuit components are employed in a pair of ocular prostheses (contact lenses or implants), each of which employs an electromagnetic field detection coil driven by a corresponding microprocessor and/or ASIC circuit processing the obtained (detected) electromagnetic signals by means of a remotely reprogrammable (and/or trainable) algorithm enabling signal detection and emission. The algorithm is configured to generate an electrical signal corresponding to the degree of desired accommodation, signal generation which improves accuracy with use over time.

In accordance with a further aspect of the proposed solution, the electronic circuitry including the coil of each eye prosthesis (contact lens or implant), and the driving algorithms, are configured to also detect changes in surrounding electrical signal activity including signal strength and phase, generated due to the activity of the neighboring coil, filter out noise according to a reprogrammable (and/or trainable) algorithm and generate an electrical signal representing the desired degree of accommodation. The filtering and signal generation is performed by means of algorithms having remotely reprogrammable parameters. Values of such parameters can be self-optimized by the patient's experience and/or by a testing procedure (preferably automated) performed at an ophthalmologist's office.

In accordance with a further aspect of the proposed solution a predetermined initial alignment of two coil sensors is used to minimize error in the generated accommodative signal.

In accordance with a further aspect of the proposed solution an accommodative learning and programming process is provided in an ocular prosthesis wherein corresponding electronic components (sensing unit, driver, battery, etc.) are internal to the ocular prosthesis (contact lens or implant). The ocular prosthesis is first worn or surgically implanted and, after a certain period of time, the prosthesis' driver's default parameters are adjusted for best accommodative experience of the patient. The patient can be asked to focus at several predetermined distances under various illumination and scene conditions, while the above mentioned coil-sensor systems are brought into a quasi-synchronized electromagnetic signal exchange (detection and emission) mode. The sources of the sensed electromagnetic signal variations at each coil sensor can be of various origins, for example due to the elements in the immediate surroundings of each eye (e.g., muscles, ions, etc.) but the most important source to be detected, in this aspect, is the electromagnetic signal emitted by the corresponding neighboring coil. An initial algorithm implementation is used to process: the detected combined electromagnetic signals, the mutual coupling strength and phases of the detected signals. This enables the generation of a drive signal representing the desired degree of accommodation with reduced error. The drive signal can be used to trigger the accommodation of the ocular prosthesis to change optical power correspondingly. After this step, a prosthesis controller of each prosthesis of the system is remotely programmed with parameters of above-mentioned signal processing algorithm to operate independently until the next ophthalmologic visit and possibly reprogramming.

In some embodiments of the proposed solution, a self-learning algorithm is provided for an ocular prosthesis (contact lens or implant) configured to accumulate a historical accommodative experience of the patient. The history includes the dynamics of electromagnetic signal detection by the controller of each prosthesis, the generation of accommodation drive signals and the final successful accommodation of the process after multiple cycles of accommodative trials. This information is then used to correct or to adjust the default parameters which are used during the signal processing, which contributes to the generation of the accommodation signal for the ocular prosthesis.

In some embodiments of the proposed solution, a reprogrammable ocular prosthesis apparatus is provided. The apparatus includes an encapsulated tunable optical device, including but not limited to a tunable liquid crystal lens, and a substantially transparent fixed optical element configured to provide a fixed optical power for augmenting the optical power of the tunable optical device. An encapsulating material is also provided enabling the overall prosthesis to contain the tunable optical device having an accommodation clear aperture, the drive signal generator, driver, controller, power storage and a sensor component arranged about the periphery of the tunable lens. A pair of encapsulated tunable optical devices includes two mutually coupled electromagnetic sensing systems including predetermined signal firing and detection as well as processing of the detected signal and determination of the degree of desired accommodation.

In some embodiments of the proposed solution, one coil generates the corresponding magnetic field during a even time period while the other coil generates the corresponding magnetic field during an odd time period, each coil employing a phase locked loop amplifier to retain synchronization with respect to the other coil.

In some embodiments of the proposed solution, each electromagnetic sensing system is configured to suppress varying magnetic fields having frequencies in the range of microsacades eye motion.

In other embodiments of the proposed solution, each electromagnetic sensing system is configured to suppress varying magnetic fields having frequencies in the range of saccades eye motion.

In yet other embodiments of the proposed solution, a frequency generated by each magnetic coil is a carrier frequency, information being carried over to the other intraocular prosthesis via varying electromagnetic fields.

While extensive reference is made herein to an intraocular vision corrective prosthesis, the invention is not limited thereto. The components and methods described herein can equally be implemented in a contact lens, and references to a prosthesis or an ocular prosthesis include intraocular lens optical devices and contact lens optical devices. Specific aspects of intraocular lenses and contact lenses may be highlighted. While extensive reference is made herein to liquid crystal tunable or variable focus lenses, the invention is not limited thereto. The components and methods described herein can equally be implemented using other designs of tunable lenses known in the art.

BRIEF DESCRIPTION OF THE DRAWINGS

The invention will be better understood by way of the following detailed description of embodiments of the proposed solution with reference to the appended drawings, in which:

FIG. 4 is a schematic diagram illustrating convergence signal transmission between cooperating intraocular tunable liquid crystal lens prostheses in accordance with the proposed solution;

FIG. 12 is schematic diagram illustrating an encapsulated tunable liquid crystal lens in accordance with the proposed solution;

FIG. 13 is schematic diagram illustrating an encapsulated tunable liquid crystal lens having a fixed optical power positive lens element deposited thereon in accordance with the proposed solution;

FIG. 14 is schematic diagram illustrating an encapsulated tunable liquid crystal lens having a fixed optical power negative lens element deposited thereon in accordance with the proposed solution;

DETAILED DESCRIPTION

In accordance with the proposed solution a vision corrective optical system having a pair of cooperative prostheses providing consorted dynamic adaptation is provided.

In accordance with the proposed solution each of a pair of tunable liquid crystal lens ocular prostheses includes an inductive coil, each inductive coil is configured to controllably generate a varying magnetic field detectable by the other inductive coil, each inductive coil is configured to detect the varying magnetic field of the other inductive coil, and to determine a degree of convergence (toe-in) and/or target object distance from the variance of the detected magnetic field.

In accordance with the proposed solution a reprogrammable ocular prosthesis apparatus is provided. The ocular prosthesis apparatus includes a tunable liquid crystal optical device encapsulated in a substantially transparent encapsulating material configured to provide a fixed optical power element for augmenting the optical power of the tunable liquid crystal optical device. The encapsulating material forms a pronounced lenticular shape at least over: an accommodation clear aperture of the tunable liquid crystal lens, the encapsulating material encapsulating the drive signal generator, driver, controller, power storage and a sensor component arranged about the periphery of said tunable liquid crystal lens. The encapsulated tunable liquid crystal optical device includes: a variable optical power tunable liquid crystal lens having an accommodation clear aperture; a tunable liquid crystal lens drive signal generator configured to generate a plurality of drive signals components, a tunable liquid crystal lens driver configured to control the drive signal generator to change the tunable liquid crystal lens optical power in response to a stimulus signal; a remote re-programmable tunable liquid crystal lens controller;

power store configured to store electrical power to drive the tunable liquid crystal lens, the driver and the controller; and a sensor component configured to provide the stimulus signal.

Tunable Optical Device System

In accordance with an embodiment of the proposed solution, the variable optical power response of a TLC lens is employed to create an ocular TLCL prosthesis with variable optical power. Optical power can be varied between a minimum and a maximum by employing a mixed frequency and amplitude control responsive to a convergence signal and preferably also responsive to at least one reprogrammable parameter.

Figure 1A:
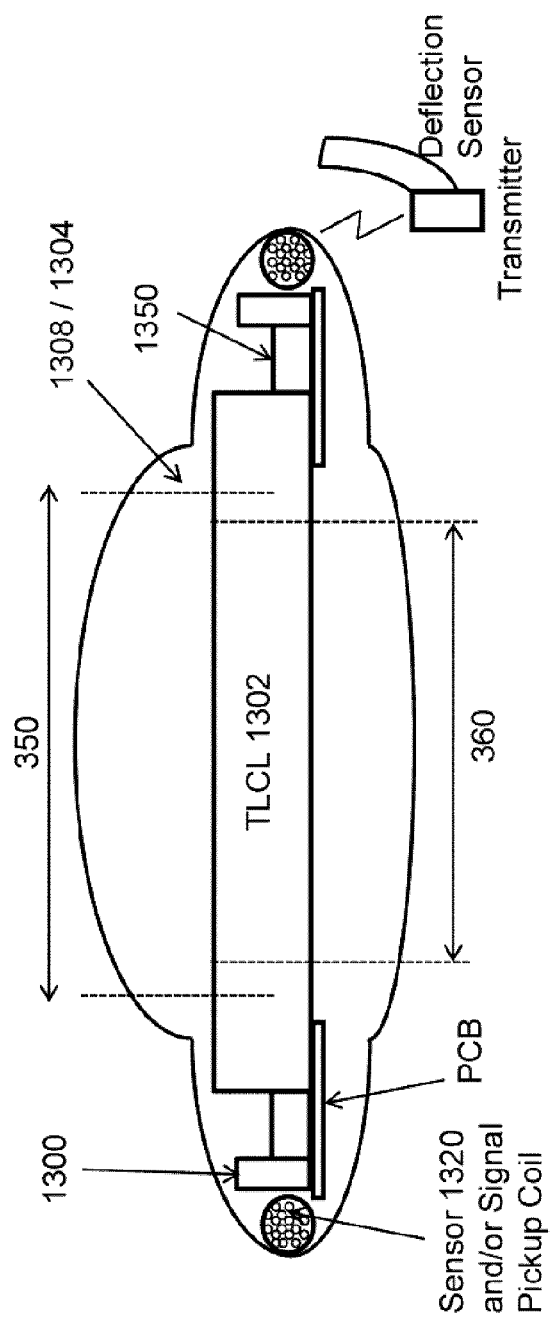
FIG. 1A is a schematic diagram illustrating a cross-section through an integral encapsulated tunable liquid crystal lens intraocular prosthesis in accordance with the proposed solution.
Figure 1C:
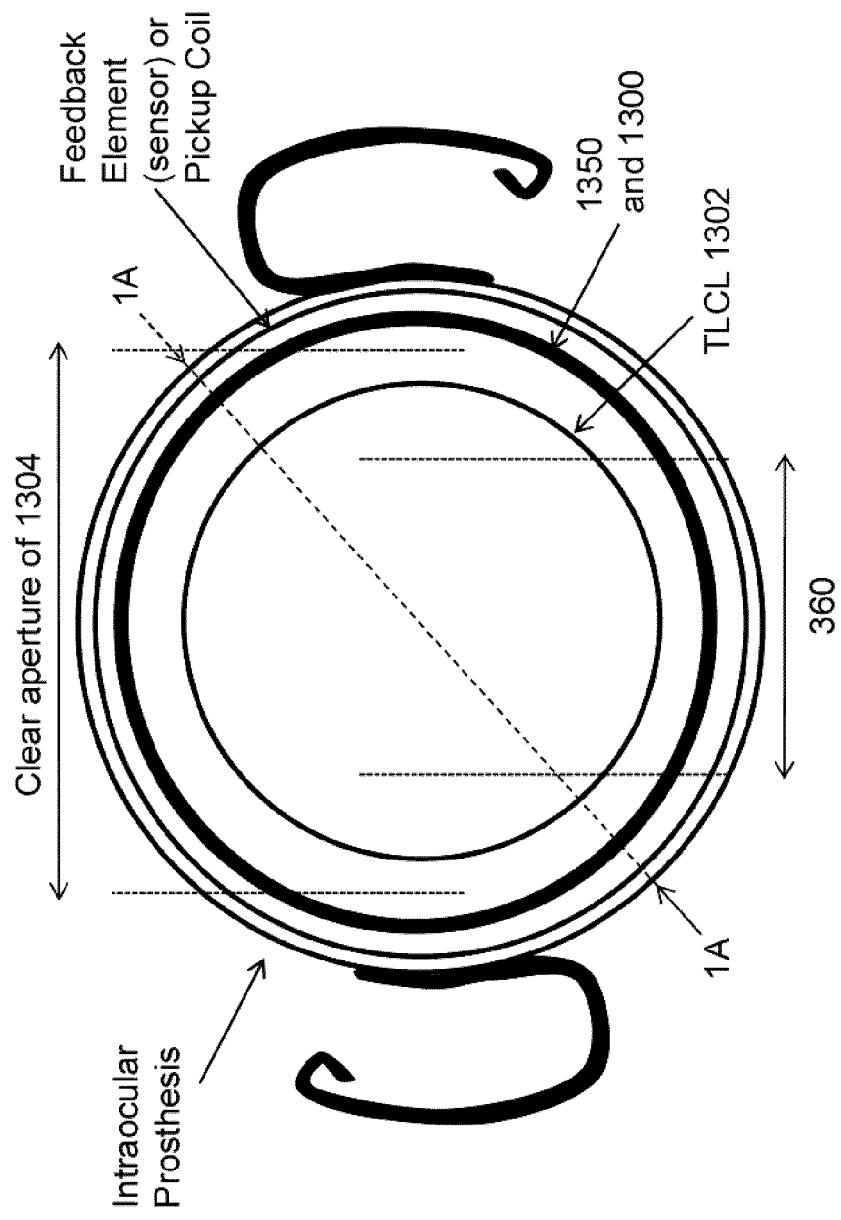
FIG. 1C is a schematic diagram illustrating a top view of an integral encapsulated tunable liquid crystal lens intraocular prosthesis in accordance with the proposed solution.
Figure 2A:
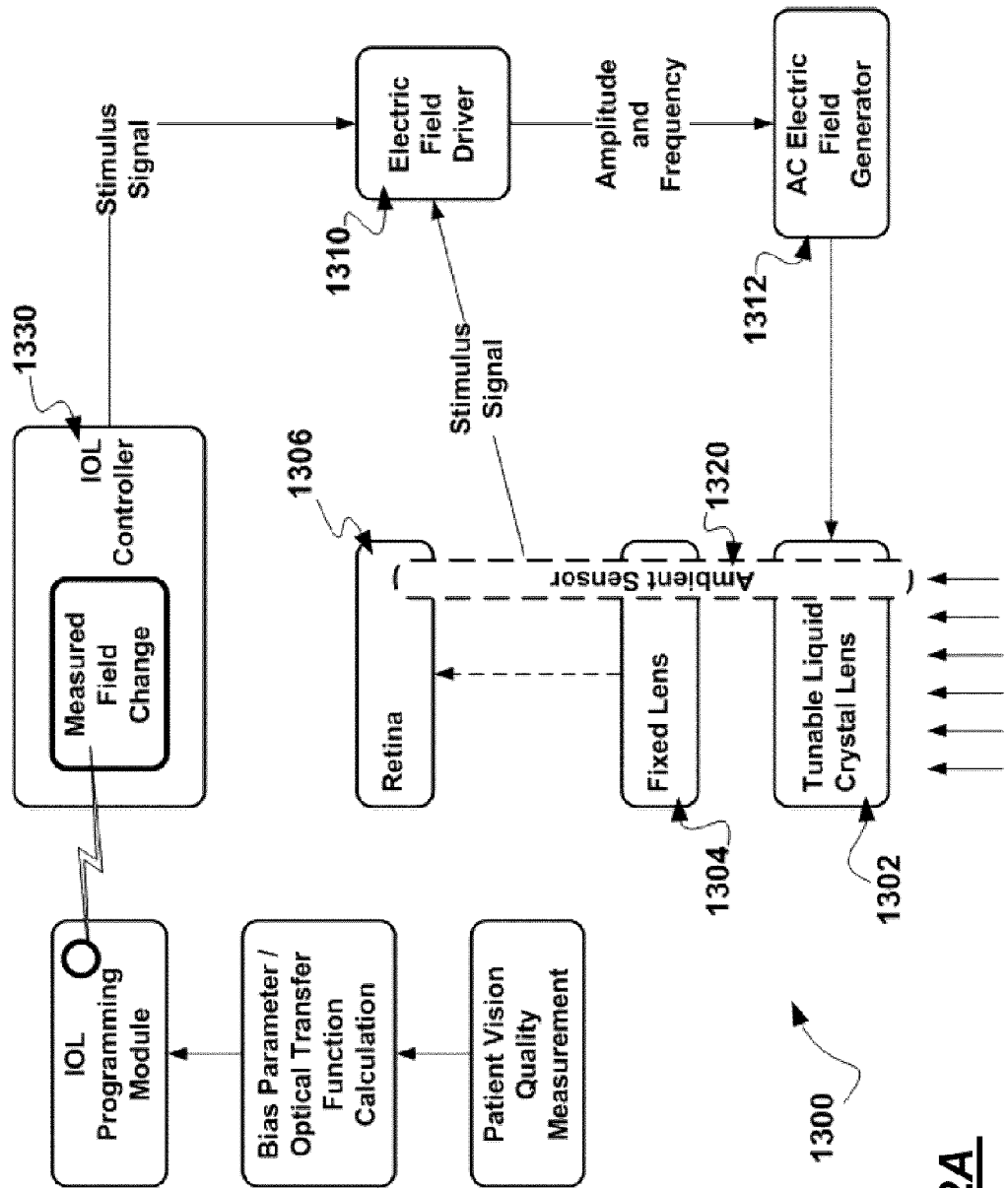
FIG. 2A is a schematic functional diagram showing interconnected tunable liquid crystal lens control components of an optical system providing assisted focus adjustment functionality in accordance with the proposed solution.

With reference to FIG. 2A, a control drive signal for tuning the TLCL can be provided by control signal electronics 1300, for example implemented in an ASIC component, configured to cause the TLCL to control light propagation as a function of at least one measured condition such as, but not limited to, convergence (azimuthal angle(s) and target distance). As an example, an ocular TLCL control system is schematically illustrated in FIG. 2A to have a TLC lens 1302 optionally combined with at least one fixed lens element 1304 to focus an image onto retina 1306 of an eye with the TLC lens 1302 providing focus control. Focusing on an image either causes a measurable change in the orientation of the eye, for example involuntary muscle tension, a physiological change caused via a voluntary (conscious) act, for example lid movement, squinting, etc. and/or a change in a convergence signal emanated from the other similarly implanted eye, for example via magnetic field coupling. A transducer can be employed to detect the physiological change. For example (FIG. 1A) a pressure, tensile, stress, etc. sensor can measure muscle compression, tension, deflection, etc. Preferably, a coil (1320) is employed to detect the convergence signal change. It is appreciated that a ciliary muscle plays a part in natural accommodation and the physiological change transducer can be configured to monitor the ciliary muscle of the eye. However, the invention is not limited to measuring physiological changes in the ciliary muscle; a variety of muscles intraocular or external can be used, for example muscles associated with the eyelid. The transducer (FIG. 1A) or an IOL controller 1330 (FIGS. 2A, 2B, 2C) provides a stimulus signal. It is appreciated that physiological changes such as squinting can be involuntary induced by a light intensity change separate from scene changes. An optional ambient (external) sensor 1320, providing an additional stimulus, can be employed to augment/correct the stimulus signal provided by the transducer and/or by the coil, for example to provide a weighting factor.

An electric field driver 1310 translates at least one stimulus into at least one electrical drive signal parameter. Without limiting the invention, the electric field driver 1310 can employ lookup tables in performing its overall function, or at least as such a translation function relates to taking into consideration empirical information regarding the TLC lens 1302 and the overall optical system 1300, including but not limited to external sensor stimuli and/or a convergence signal. For an intraocular TLCL prosthesis replacing the natural lens, the external sensor 1320 can be configured to take into consideration the effect of the variable iris of the eye and/or the electric field driver 1310 can be configured to take into account typical time variant iris variability (for example time variant calibration curves can be employed via lookup tables). For example time variant natural iris variability information can be employed to adjust the response of the electric field driver 1310 to prevent positive feedback situations unnecessarily driving the TLCL lens to extremes. It is expected that the natural reaction of the natural iris (and the nervous system controlling the iris) is plastic and that the iris will also react to operational particulars of such a TLCL intraocular implanted prosthesis. The ambient sensor 1320 is illustrated in FIG. 2A to be in the optical path, for example behind the iris. The invention is not limited to a TLCL intraocular prosthesis replacing the natural lens of the eye, implantation of a TLCL in other eye cavities places the TLCL either in front or behind the iris and therefore the location of the ambient sensor 1320 can vary accordingly. As another example, the physiological change sensor and/or ambient sensor 1320 can be replaced by an image sensor pointed towards the retina of the eye and receiving backscattered light from the retina. With only a limited number of pixels, such an imaging sensor can be configured to detect sharpness in an image projected onto the retina, the image sensor proving a focus score as a stimulus signal. In some implementations, the sensor 1320 includes the coil of IOL controller 1330.

An electric field generator 1312 converts the electrical drive signal parameters into at least one drive signal to be applied to the TLCL 1302. Those skilled in the art may appreciate that component 1310, without limiting the invention, can be implemented using microcode executed on a microcontroller, while component 1312 can include voltage sources switched under the control of a microcontroller to provide a resulting drive signal of desired frequencies and RMS voltages. Such a microcontroller can be configured to obtain stimuli and/or a convergence signal and determine drive signal parameters to operate the TLCL 1302 to change optical power towards best focus. For example best focus can be asserted by detecting minimal stimulus signal change below a threshold. Frequency signal generators are known, and only limited details are provided herein with respect to employing such a frequency signal generator to implement a TLCL control component of the tunable optical system.

In accordance with the proposed solution, there is provided an ocular lens controller 1330 configured to control the operation of the electric field driver 1310. The ocular lens controller 1330 is preferably reprogrammable and can include a remote programming interface via which electric field driver 1310 parameters can be changed. For example an ophthalmologist or optometrist can, over the remote programming interface, interrogate the ocular lens controller 1330 (and/or the electric field driver 1310) for operational parameters and/or set operational parameters. For certainty, manual intervention of an ophthalmologist or optometrist is not required. Interrogating the ocular lens controller 1330 and setting operational parameters can be automated, and manual operation by ophthalmologist or optometrist can be limited to initiating such processes at the appropriate time.

In some implementations the ocular lens controller 1330 programming interface has a dedicated antenna, in other implementations the programming interface shares an existing antenna on the ocular device, for example a (ambient) sensor pickup coil or a coil employed by recharge electronics. Re-programming of an intraocular lens controller 1330 enables long term and repeated adaptation of the intraocular device to account for eye aging, plasticity, uneven healing, etc. effects experienced postoperatively. Such adjustments can be rewritten with subsequent reprogramming (under the supervision of an ophthalmology professional).

In accordance with an implementation of the proposed solution, an inductive coil, for example associated with the recharge electronics of the ocular TLCL prosthesis, is employed to transmit a known signal to a second ocular TLCL prosthesis of (implanted in) the other eye, and to receive a known signal via electromagnetic coupling from the other prosthesis, wherein deviations from an expected (known/learned) signal correspond to eye convergence at a particular distance at which each variable ocular TLCL prosthesis is to be focused.

Figure 2B:
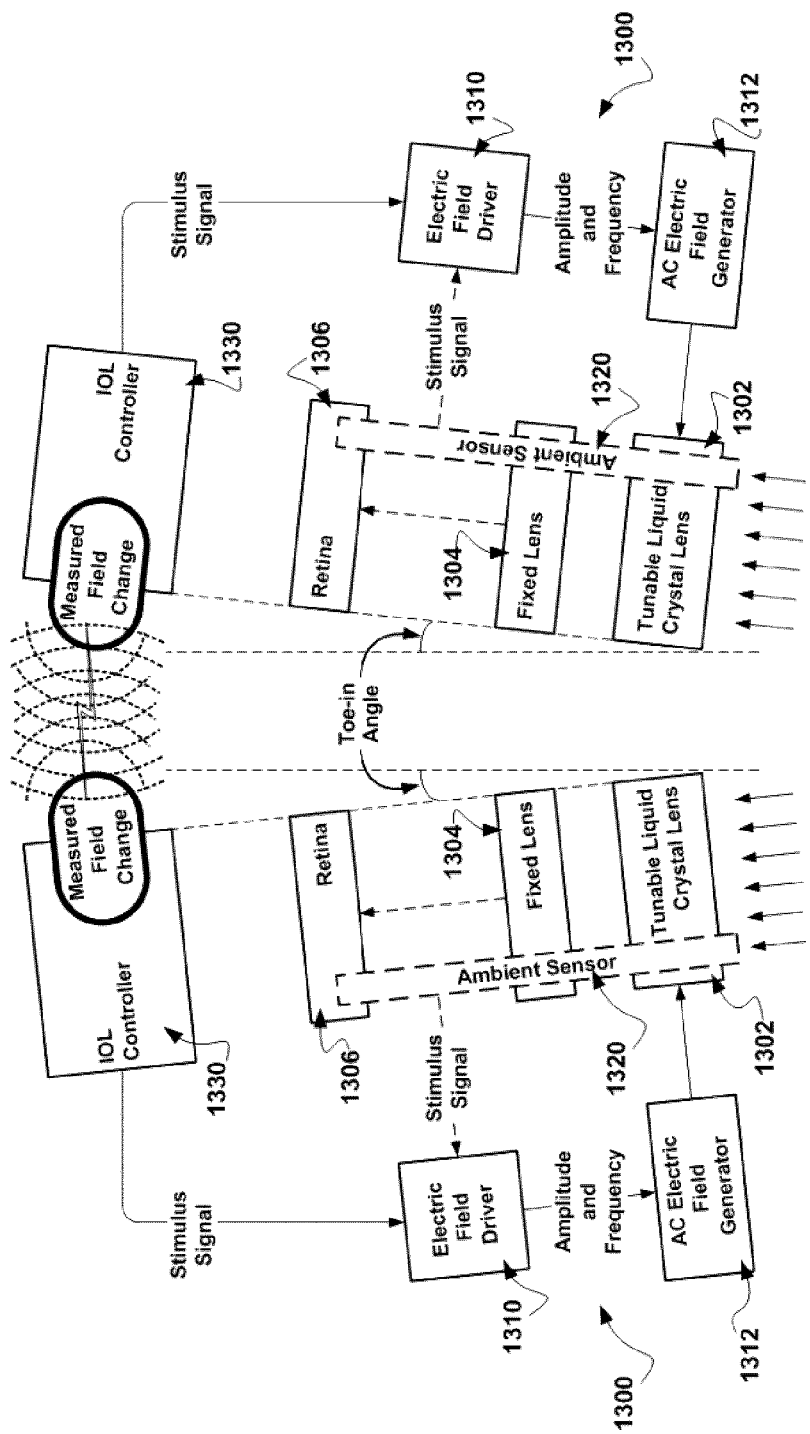
FIG. 2B is a schematic functional diagram showing cooperating intraocular tunable liquid crystal lens prostheses control components of an optical system providing assisted focus adjustment functionality in accordance with the proposed solution.
Figure 3A:
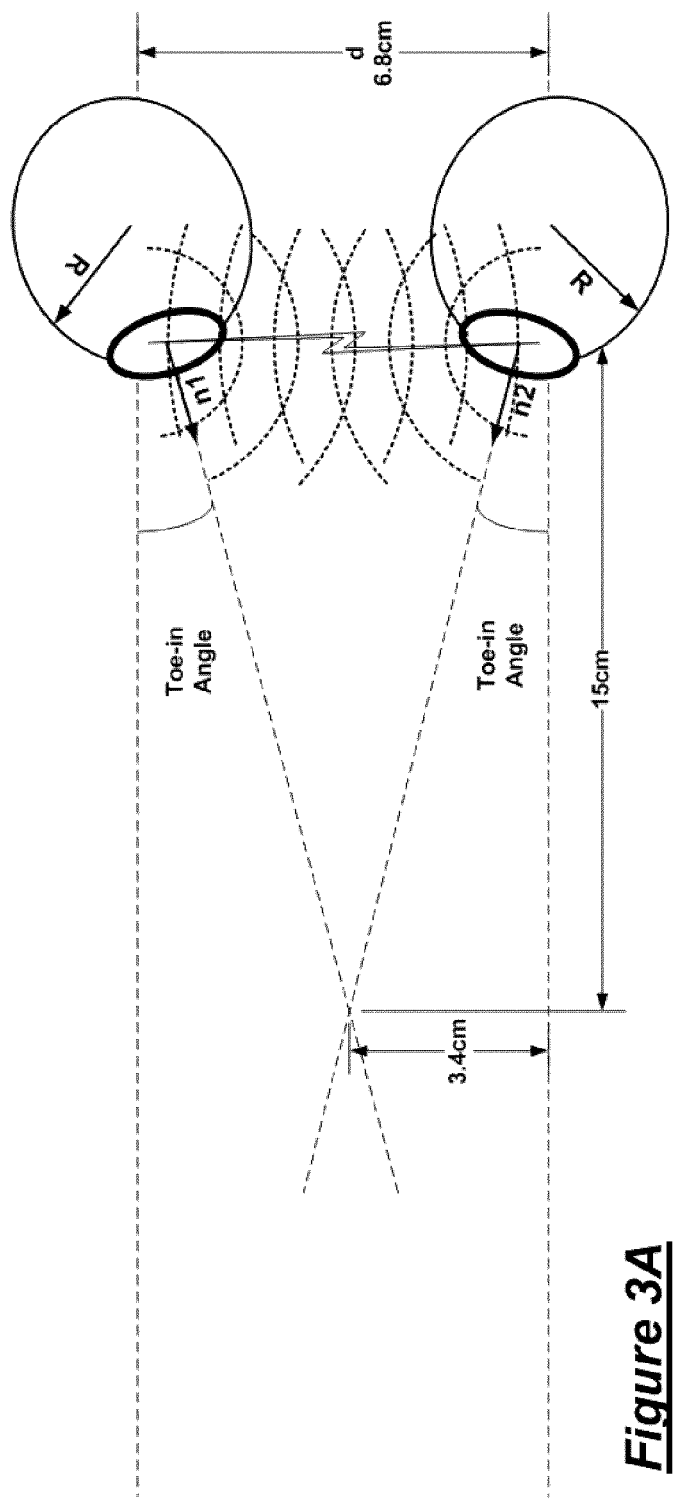
FIG. 3A is a schematic diagram illustrating an optical system employing cooperating a pair of intraocular tunable liquid crystal lens prostheses in accordance with the proposed solution.
Figure 3B:
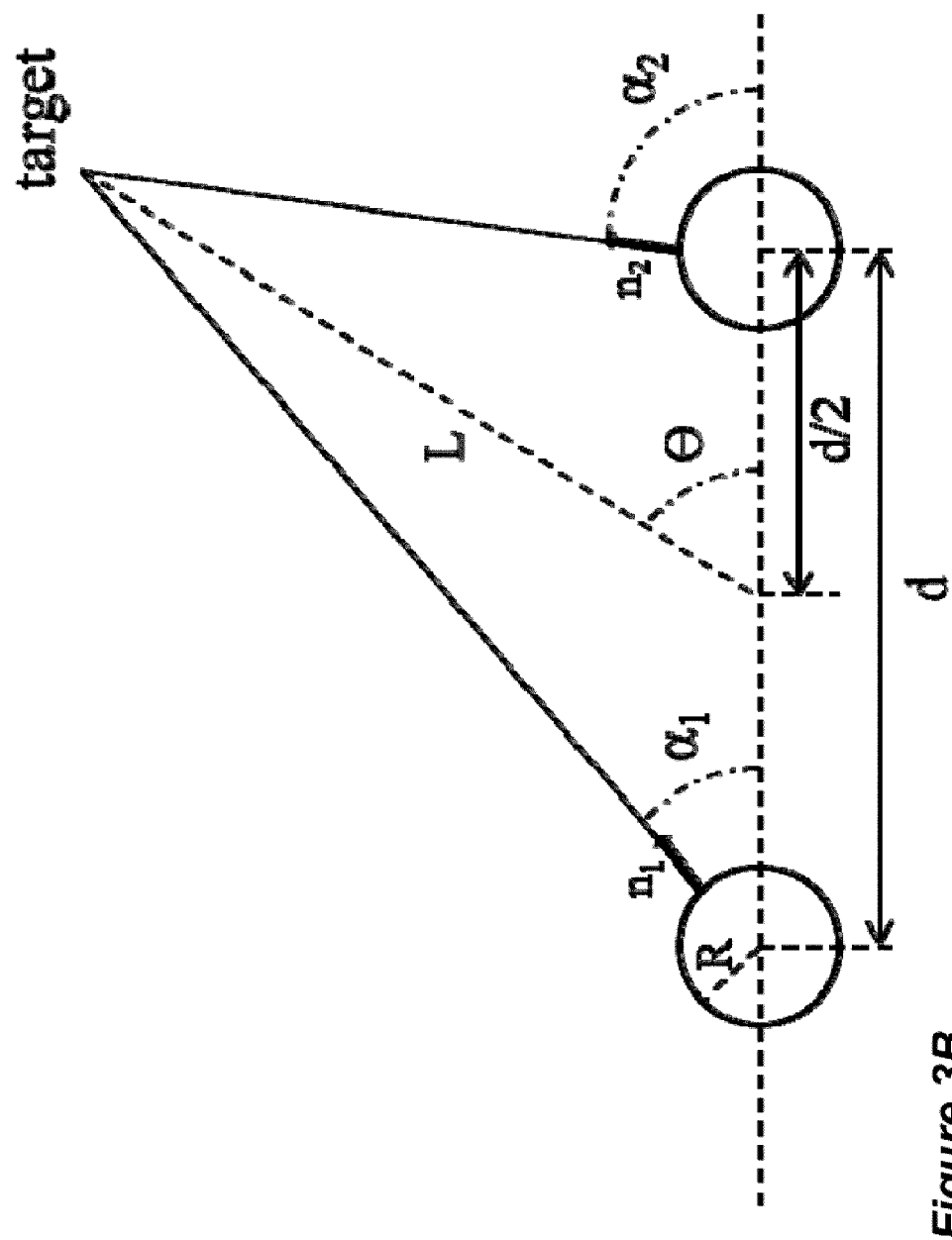
FIG. 3B is a schematic diagram illustrating variables employed in implementing signal detection algorithms in accordance with the proposed solution.

With reference to FIG. 2B an ocular prosthesis is associated with each eye wherein the coil is employed to sense a toe-in angle, or collectively to sense the convergence angle of the eyes, to provide the stimulus signal. For example, the ocular TLCL controller 1330 uses the inductive coil to generate an electromagnetic field and to measure a change in the electromagnetic field emanated by the other ocular TLCL controller 1330 inductive coil. With reference to FIG. 3A, when the eyes are focused at infinity, the optical axes $n_1$, $n_2$ of the eyes are parallel. When the eyes are directed at object closer than infinity, each eye is oriented with a certain degree of toe-in $\alpha_1$, $\alpha_2$; such that both eyes define an angle of convergence therebetween. The required focal distance, and hence the corresponding optical power necessary to focus each eye onto the object, has a monotonic relationship with the convergence angle between the eyes at least for a fixed azimuthal angle and fixed attitude angle of the object with respect to an on-axis forward direction with respect to the interpupilary axis (FIG. 3A). In some implementations each coil measures electromagnetic field strength. In other implementations the coils have a high quality factor and phase differences in the received electromagnetic signal are considered in determining a degree of eye toe-in or convergence between the eyes. For example, FIG. 3A illustrates typical dimensions of the combined optical system with a generic 6.8 cm interpupilary distance. For a generic 15 cm closest focus provided by each intraocular prosthesis, the toe-in angle is given by arctan(3.4 cm/15 cm) or about 12.8° toe-in. The corresponding maximum on-axis convergence angle is about 25.5°. Off-axis convergence, is illustrated in FIG. 3B, employs more complex trigonometric relationships as described hereinbelow.

FIG. 4 schematically illustrates the generation of the convergence signal. For example, each ocular prosthesis emanates a known signal (akin to a ping) in a corresponding one of an odd and even time window. In some embodiments, however without limiting the invention, the transmitted signal envelope is square with a small duty cycle to reduce power consumption. The (ping) convergence signal propagates through the human body between the eyes, and trough the air, and arrives at the other ocular prosthesis having a modified envelope (not necessarily as shown). A phase locked loop amplifier can be employed to extract window timing information from the received signal envelope. It is expected that the envelope may be retarded by a phase amount which can be employed in determining the convergence angle along with the strength of the electromagnetic field.

FIG. 4 illustrates transmitting a sinusoidal convergence signal from one ocular prosthesis to the other. At least two implementation modalities are possible. In some implementations, the transmit frequency can be generated in one ocular prosthesis with a high quality factor and the other ocular prosthesis can determine departures from the known transmit frequency. In other implementations, the receiving ocular prosthesis filters out frequencies between 30 Hz and 70 Hz except during the listening windows, as the "transmitting" ocular prosthesis simply jitters at between 30 Hz and 70 Hz in well documented involuntary eye microsaccade motion providing a magnetic field variance in a receiving coil without specific electromagnetic signal generation at the transmitting coil benefiting from reduced operating power. Typical microsaccade motion amplitude is 0.2° but can vary between 0.03° to 2° (2 to 120 arcmin).

Figure 2C:
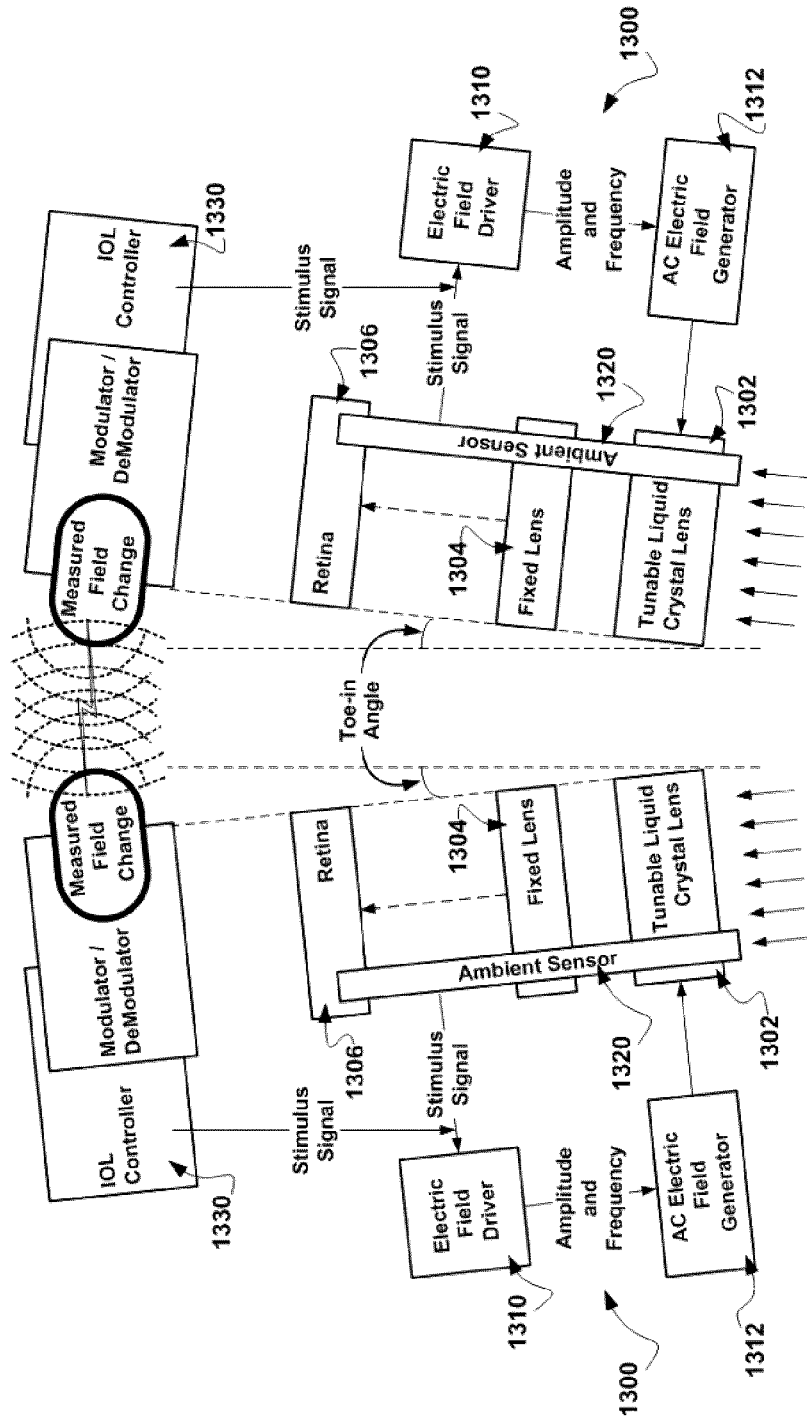
FIG. 2C is a schematic diagram illustrating communications between two intraocular prostheses in accordance with the proposed solutions.
Figure 2D:
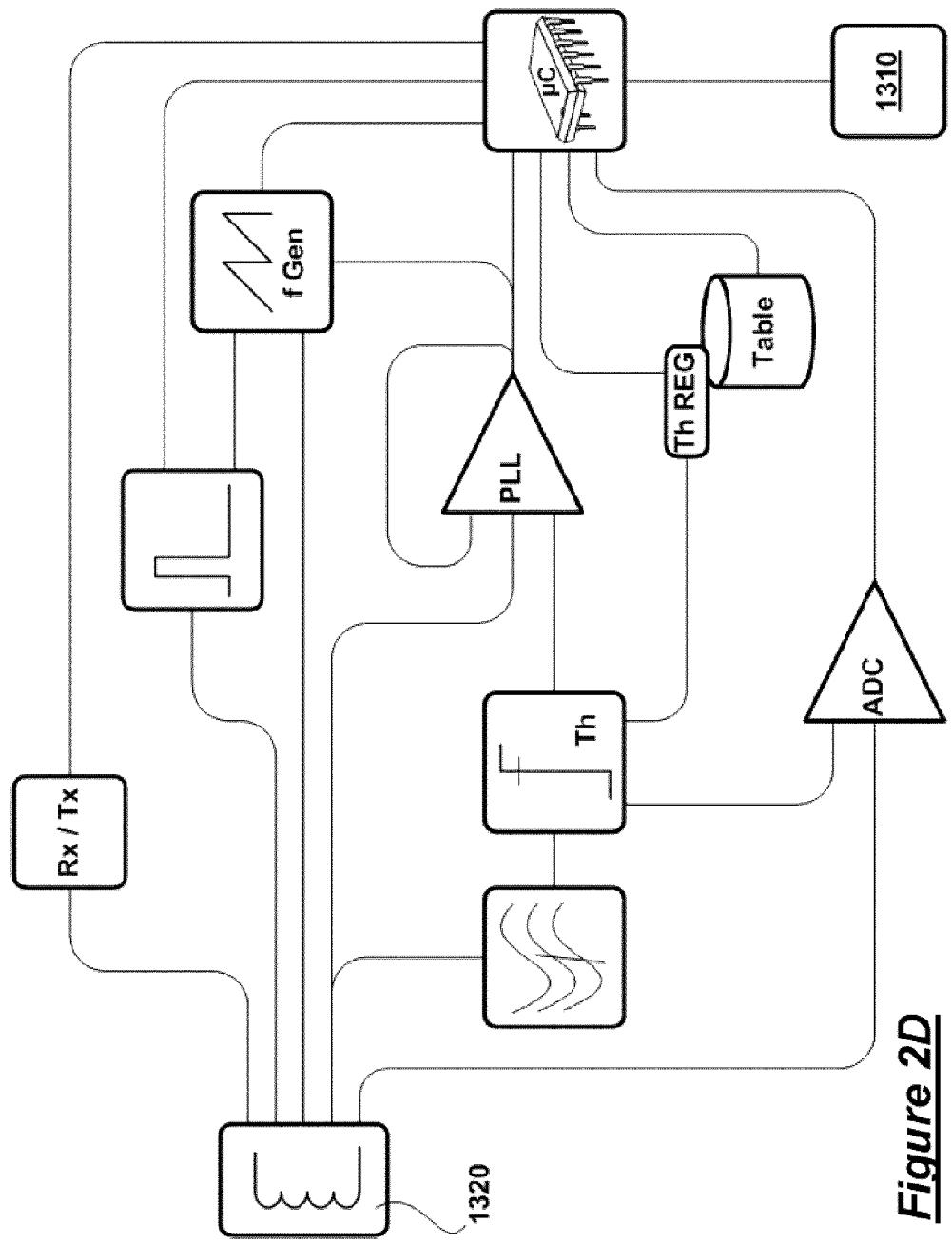
FIG. 2D is a schematic circuit diagram illustrating components of a controller in accordance with the proposed solution.

FIG. 2D schematically illustrates components of a generalized IOL controller circuit 1330. The IOL controller 1330 circuit includes a variety of analog and digital components. Coil 1320 receives an electromagnetic signal from the coil of the other ocular prosthesis. The received signal is fed at least to a phase locked loop (PLL) amplifier to extract window timing information which is provided at least to a microcontroller.

In some implementations the convergence signal includes a train of electromagnetic pulses. The IOL controller 1330 feeds the signal received by coil 1320 to a high frequency band pass filter for isolating each pulse from the signal received. A signal threshold trigger (Th) filters the high frequency signal from the high band pass filter to provide a trigger signal. The threshold can be set by the microcontroller with a value stored in a threshold register (Th REG). The trigger signal is provided to an EMF sampler, including an Analog to Digital Converter (ADC) which provides the microcontroller with EMF sample values. The trigger signal is also provided to the microcontroller, directly or via the PLL amplifier, to cause the microcontroller to read the EMF sample values from the output of the EMF sampler. The microcontroller can store multiple EMF sample values for processing. Providing the trigger signal to the PLL amplifier enable extraction of windowing timing information. For convergence signal transmission, the microcontroller instructs a frequency generator (f Gen) to generate a pulse trigger frequency. The frequency generator can employ windowing timing information provided by the PLL amplifier to time the pulses (delay) to avoid transmit/receive collisions. For certainty the PLL amplifier is not required in this implementation as the trigger signal can be provided to the frequency generator, perhaps with a time delay, to the frequency generator. The signal produced by the frequency generator, at a pulse rate, is provided to a pulse generator which can be instructed by the microcontroller to drive the coil 1320 to output pulses of a controlled amplitude and duration (which are configurable parameters).

In other implementations, the convergence signal includes a signal having a frequency (FIGS. 9, 10 and 11) and an envelope (FIG. 4) defining window timing. The coil 1320 provides the received signal to the PLL amplifier which extracts the window timing information. The received signal is also provided to the EMF signal sampler, the EMF sample value output of which is read by the microcontroller during the receive window specified by the PLL amplifier at a sampling rate sufficient to take into account microsaccades motion of the eyes. The window timing information is also provided to the frequency generator to initiate convergence signal transmission at transmit times appropriately delayed as not to coincide with signal reception from the other ocular prosthesis. The output of the frequency generator can be configured by the microcontroller to have a specific envelope (for example square).

In accordance with the proposed solution, multiple EMF sample values are processed 812, 816 by the microcontroller which subsequently provides the electric field driver 1310 with a stimulus signal. Typically the microcontroller performs at least one table lookup 812 in at least one table to determine at least a target object distance. The microcontroller can also determine an azimuthal target angle in the process. The stimulus signal is indicative of the patients desired accommodation.

Convergence Detection

In accordance with the proposed solution, the principle of operation of the above described systems and components include an electromagnetic detection system based on two active coils (one per ocular prosthesis) operating both in reception (detection) or emission (signal impulse ping, firing transmit frequency, carrier transmission) modes. In addition, the emission (firing, ping, carrier) and detection processes are controlled by a microprocessor (ASIC, for example controller 1330) and algorithm, which can be reprogrammed in time or improved through a continuous self-optimization process.

For brevity, the operation of simple coupled coils (or loops) and their mutual coupling is described first followed by details of the rest of operation of the system and components. For example in Robinson, P. R., "Improvements to the System of Four Equiradial Coils for Producing a Uniform Magnetic Field," J. Phys. E: Sci. Instrum. 16, 39-42, 1983, which is incorporated herein by reference, the magnetic field (in Tesla units) of a magnetic dipole at a distance $\vec{r}$ can be expressed as:

$$\vec{B}(\vec{r}) = (\mu_0/(4\pi))(3(\vec{r}\cdot\vec{m}_1)\vec{r}/r^5 - \vec{m}_1/r^3) \quad \text{Eq. 1}$$

where $\vec{m}_1$ is the magnetic moment of the current loop which forms the dipole and is equal to:

$$\vec{m}_1 = I\vec{s}_1 = I\pi b^2 \vec{n}_1 \quad \text{Eq. 2}$$

where b is the radius of the coil, $S_1$ is the surface of the coil, $\vec{n}_1$ is a unit vector perpendicular to the plane defined by $S_1$, and I is the current in the coil.

The magnetic flux (in Weber units) through the second coil having the same radius b as the first coil may be expressed as:

$$\Phi = \vec{B}\cdot\vec{S}_2 = \vec{B}\pi b^2 \vec{n}_2 \quad \text{Eq. 3}$$

where $\vec{n}_2$ is a unit vector perpendicular to the plane defined by the surface $S_2$ of the second coil. The magnetic flux is related to the mutual inductance M through the equation:

$$\Phi = MI. \quad \text{Eq. 4}$$

By combining Eqs. 1 to 4, the following relation is obtained for the mutual inductance in Henry units (note that pH stands for $10^{-12}$ H) between the two current coils:

$$M = (\mu_0 \pi b^4/(4d^3))(3\sin^2\theta - \cos(2\theta)) \quad \text{Eq. 5}$$

where θ is the toe-in angle between the line of sight and the pupillary axis and d is the interpupillary (eye-to-eye) distance between the pupil centers as shown in FIG. 3A for on axis convergence. (Note that for on-axis convergence the toe-in angles are equal as illustrated in FIG. 3A, for off-axis convergence the toe-in angles are different as illustrated in FIG. 3B.)

Taking into account that the interpupillary distance changes along with θ because of the coil is displaced from the center of eyeball rotation, eyeball radius R=D/2, the on-axis mutual induction relation becomes:

$$M = (\mu_0 \pi b^4/(4(d-2R\sin\theta)^3))(3\sin^2\theta - \cos(2\theta)). \quad \text{Eq. 6}$$

Figure 5:
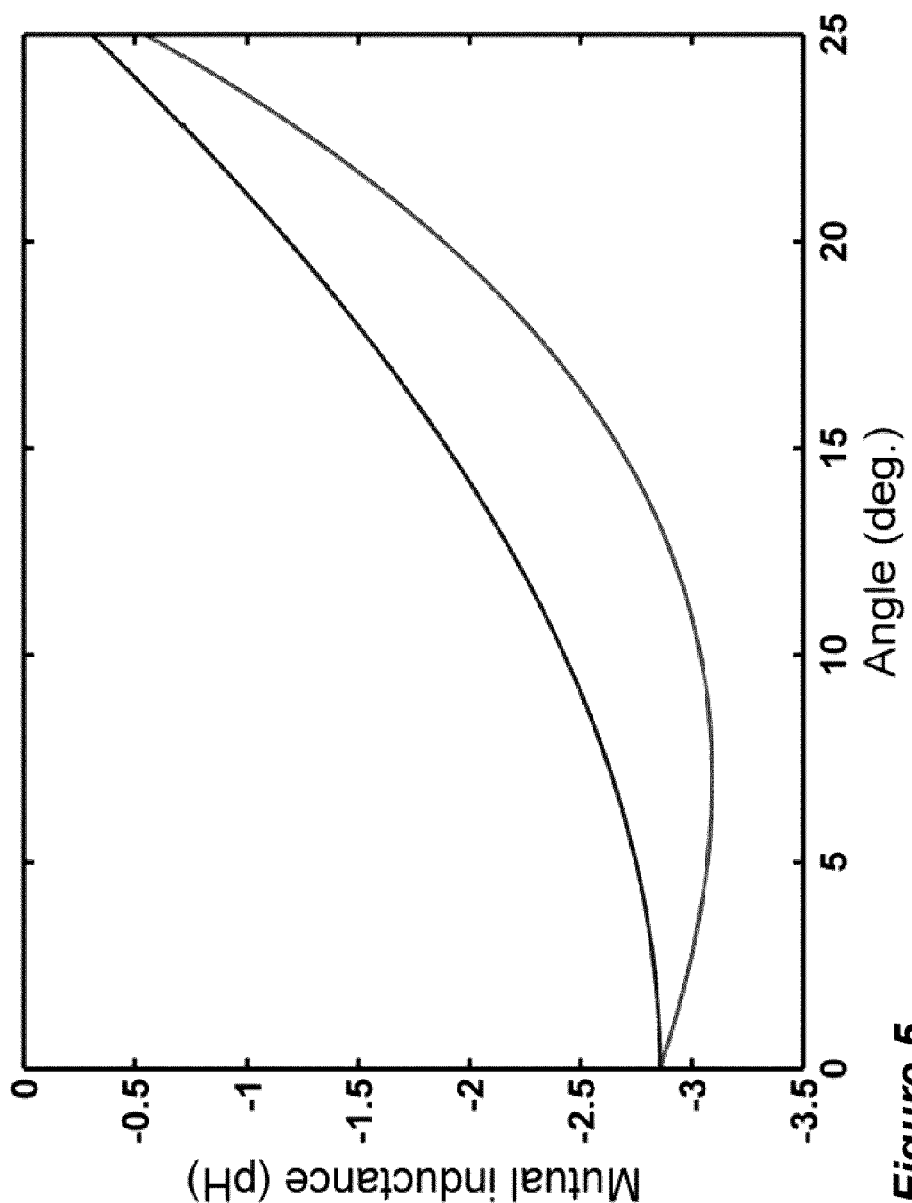
FIG. 5 is a schematic plot illustrating the mutual inductance during the accommodation effort for angular tilt only (upper curve) and for angular tilt with spatial movement of the eyes, respectively in accordance with the proposed solution.

FIG. 5 numerically illustrates the on-axis mutual inductance between two coils, target object azimuthal angle of zero (right in front), as a function of the toe-in angle θ calculated using Eq. 5 for the upper curve and Eq. 6 for the lower curve. The result, which is the most representative to how the actual mutual inductance would be measured/sensed, is represented by Eq. 6 lower curve. The curve first decreases slightly and then increases noticeably for the same tendency of angular convergence. This means that for some starting distances an accommodation request associated with the mutual angular convergence angle of the two eyes might create some confusion in signal processing with respect to whether the eyes are converging or diverging. Namely, from infinity (zero degree toe-in) to approximately 25 cm (approximately 7° toe-in), the mutual inductance decreases monotonically. Despite the fact, the change (in mutual coupling is relatively small) we might use this reduction as a signal (request) to accommodate to shorter distances. This would be acceptable if the minimal distance of accommodation would be 25 cm as there is no ambiguity in the mutual inductance values for viewing distances between 25 cm and infinity (0°), which already constitute an appreciable working range.

Figure 6:
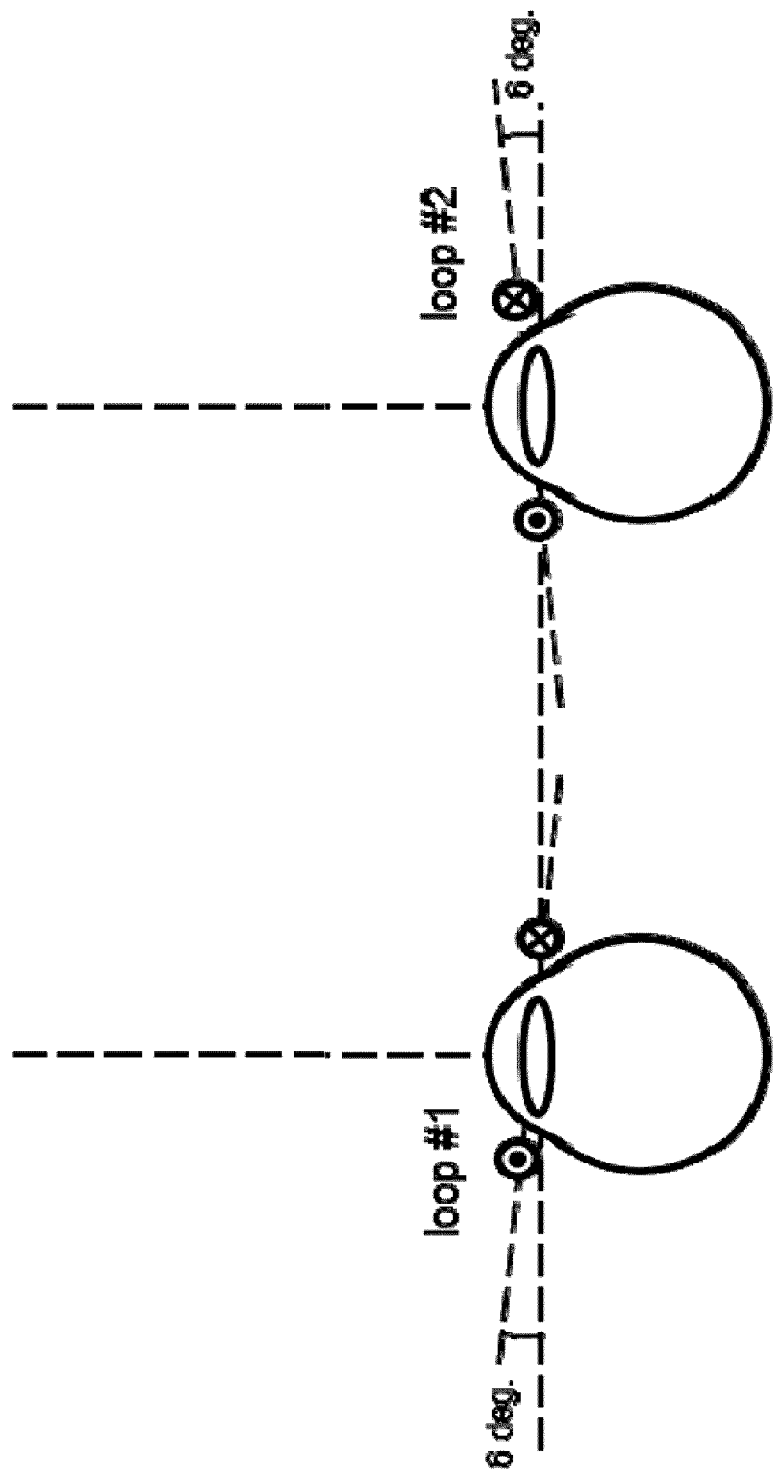
FIG. 6 schematically illustrates employing a relative tilt difference between the two coils in accordance with the proposed solution.
Figure 7:
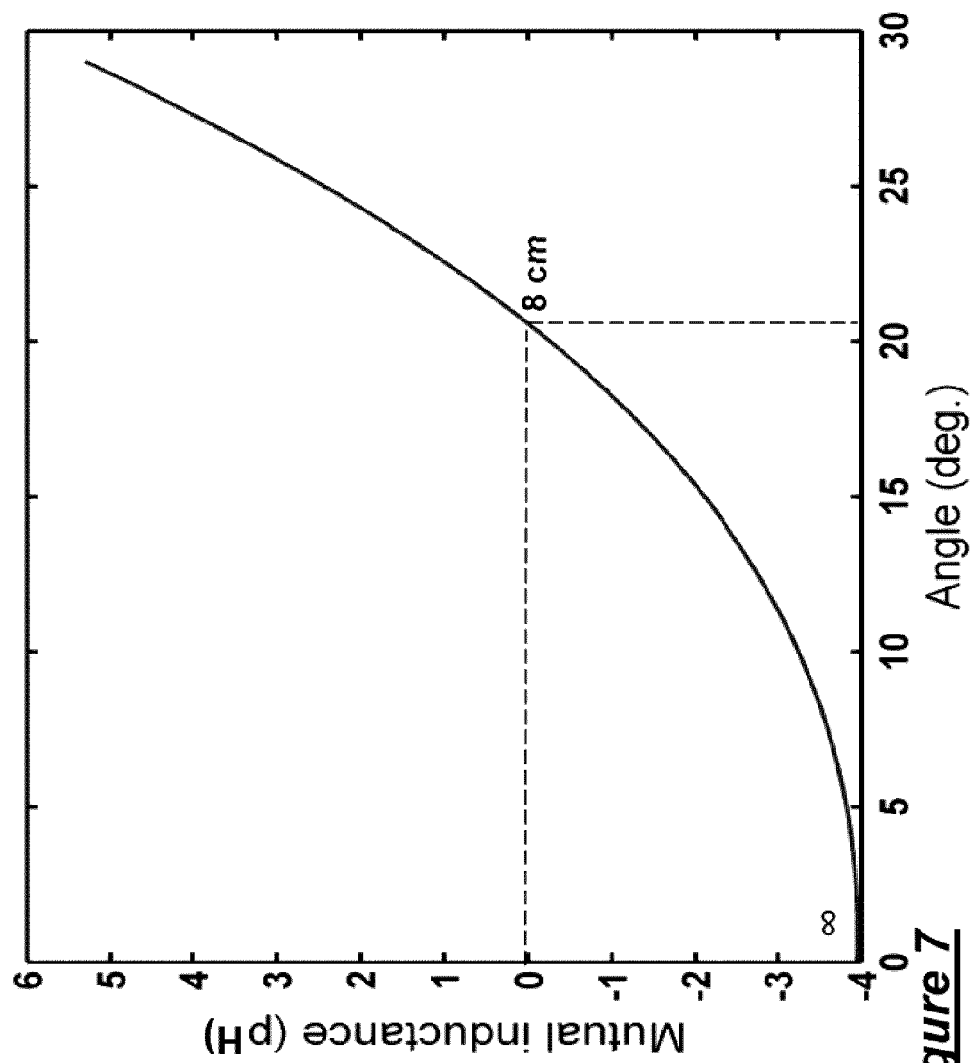
FIG. 7 is a schematic plot illustrating mutual inductance employing an angular offset to eliminate the ambiguity illustrated in FIG. 5 in accordance with the proposed solution.

However, if the patient needs to focus closer, then the eyes will further converge while the mutual inductance will start to increase instead of continuing the initial decrease (so the tendency of the signal will be inversed) leading to the signal processing confusion. In accordance with the proposed solution, the associated difficulty of signal processing can be reduced by adding an initial relative tilt (azimuthal shim) between the two coils at the 0° toe-in angle (at infinity focus). FIG. 6 illustrates a configuration where a 12° total tilt difference between the coils is introduced. The calculated mutual induction, for the configuration illustrated in FIG. 6 reverses its sign for distances less than 8 cm as illustrated in FIG. 7. Finally, it can be appreciated also that the slope of change is now steeper, which would help to reduce error in discerning the accommodation signal. One of the advantages of the proposed implementation is that the mutual inductance represents (for example through a correspondence table) the convergence angle without a need to additionally communicate convergence information about the absolute angular orientation of an eye to the corresponding other eye. That is, there is no need for employing gyroscopes and related circuitry.

While the above relate to on-axis convergence, it is understood that off-axis convergence (target object to the side) is subject to ambiguity in signal processing. FIG. 3B illustrates variables employed in implementing generalized signal detection algorithms in accordance with the proposed solution for off-axis convergence in a horizontal plane (attitude angle zero, eyes have the same attitude angle) on a target object at a distance L from center having an azimuthal angle θ from center. Note this change in the definition of the angle θ, the original angle θ for on-axis convergence is replaced by different toe-in angles $\alpha_1$ and $\alpha_2$. Dependencies of $\alpha_1$ and $\alpha_2$ on azimuthal angle θ and target distance L can be expressed as:

$$\tan(\alpha_1) = \frac{L\sin(\theta)}{d/2 + L\cos(\theta)}, \text{ and } \tan(\alpha_2) = \frac{L\sin(\theta)}{d/2 - L\cos(\theta)}.$$

The generalized mutual inductance relation Eq. 6 taking into account azimuthal angular displacement becomes:

$$M = \frac{\mu_0 \pi b^4}{4}\left[\frac{3}{r^5}(R + d\cos(\alpha_2) - R\cos(\alpha_1 - \alpha_2))\right.$$
$$\left.(d\cos(\alpha_1) - R + R\cos(\alpha_1 - \alpha_2)) - \frac{1}{r^3}\cos(\alpha_1 - \alpha_2)\right],$$

-continued where $$r = \sqrt{(d + R\cos(\alpha_2) - R\cos(\alpha_1))^2 + R^2(\sin(\alpha_2) - \sin(\alpha_1))^2}$$

Figure 8A:
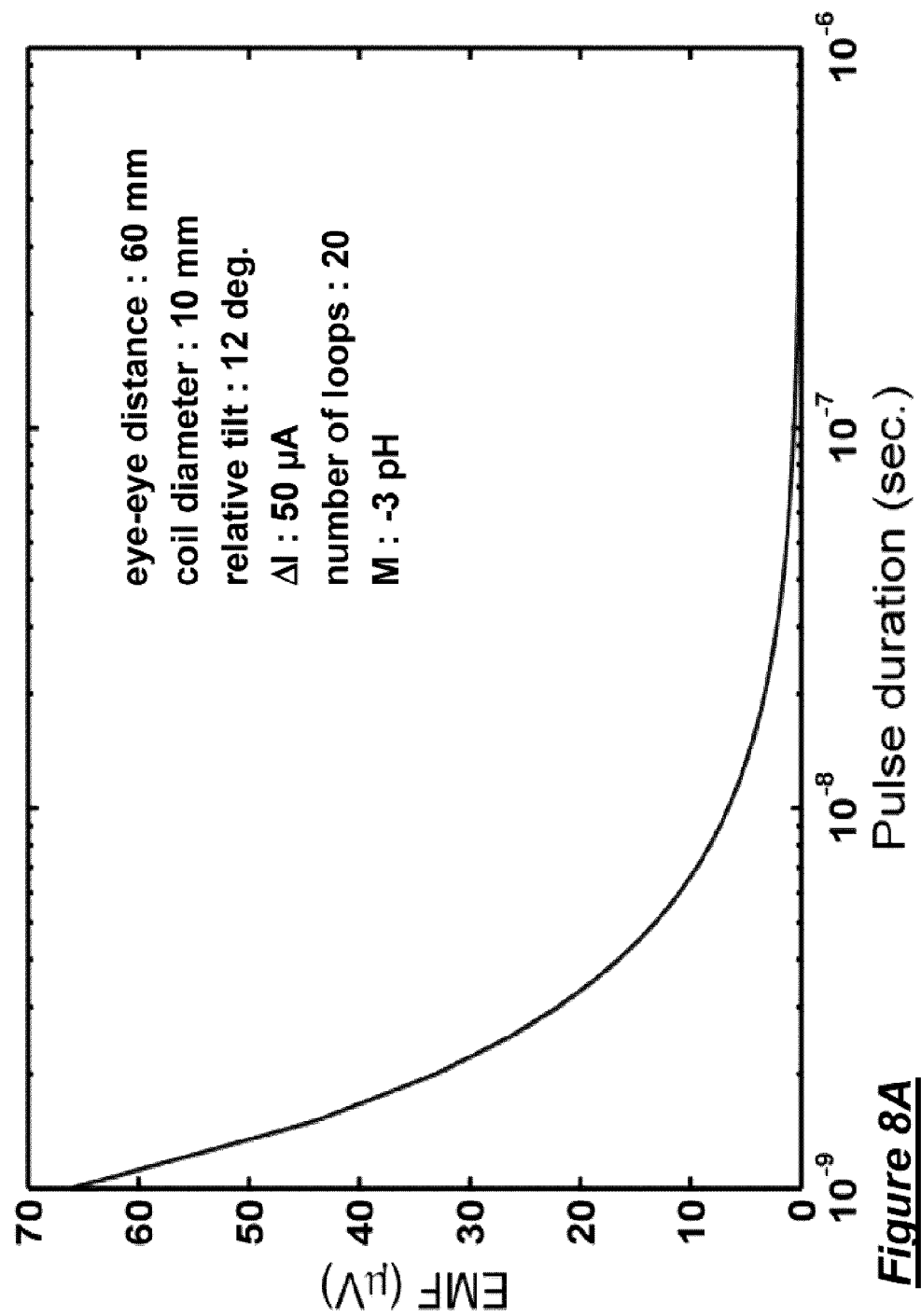
FIG. 8A is a schematic plot illustrating the induced EMF as a function of current pulse duration for 50 μA pulses and coils as illustrated in FIG. 7 having 20 loops in accordance with the proposed solution.

The energetic aspect of the proposed sensing system requires consideration. The temporal variation of the current in the transmitting coil will induce an EMF (ElectroMotive Force in Volts units) in the corresponding other receiving coil following the relation:

$$EMF = -N^2 \Delta\Phi/\Delta t = -N^2 M \Delta I/\Delta t \qquad \text{Eq. 7}$$

where N is the number of turns in each coil, $\Delta I$ is the variation of the current and $\Delta t$ is the duration of time for which the $\Delta I$ happened. Two parameters can be used to increase the overall performance of signal detection in the system, the number of turns of each coil N and the ratio of $\Delta I/\Delta t$ (ping, frequency variation, etc.). It would be desirable to keep the values of $\Delta I$ as low as possible (power of the ping, driving power). For the sake of estimation, if the $\Delta I$ is in the range of a few tenths of microamperes, then electrical pulses (ping or duty cycle) of few microseconds (ping duration) should be considered to keep the value for the ratio of $\Delta I/\Delta t$ in a reasonable range from a power perspective. Because the EMF is proportional to the time derivative of the current change, the EMF signal in the detecting ocular prosthesis will be 90° out of phase to the driving signal in the (emitting and) detecting ocular prosthesis. FIG. 8A illustrates a plot of typical on-axis computed EMF values as a function of $\Delta t$ for $\Delta I=50$ µA and a mutual inductance of -3.3 pH.

Figure 8B:
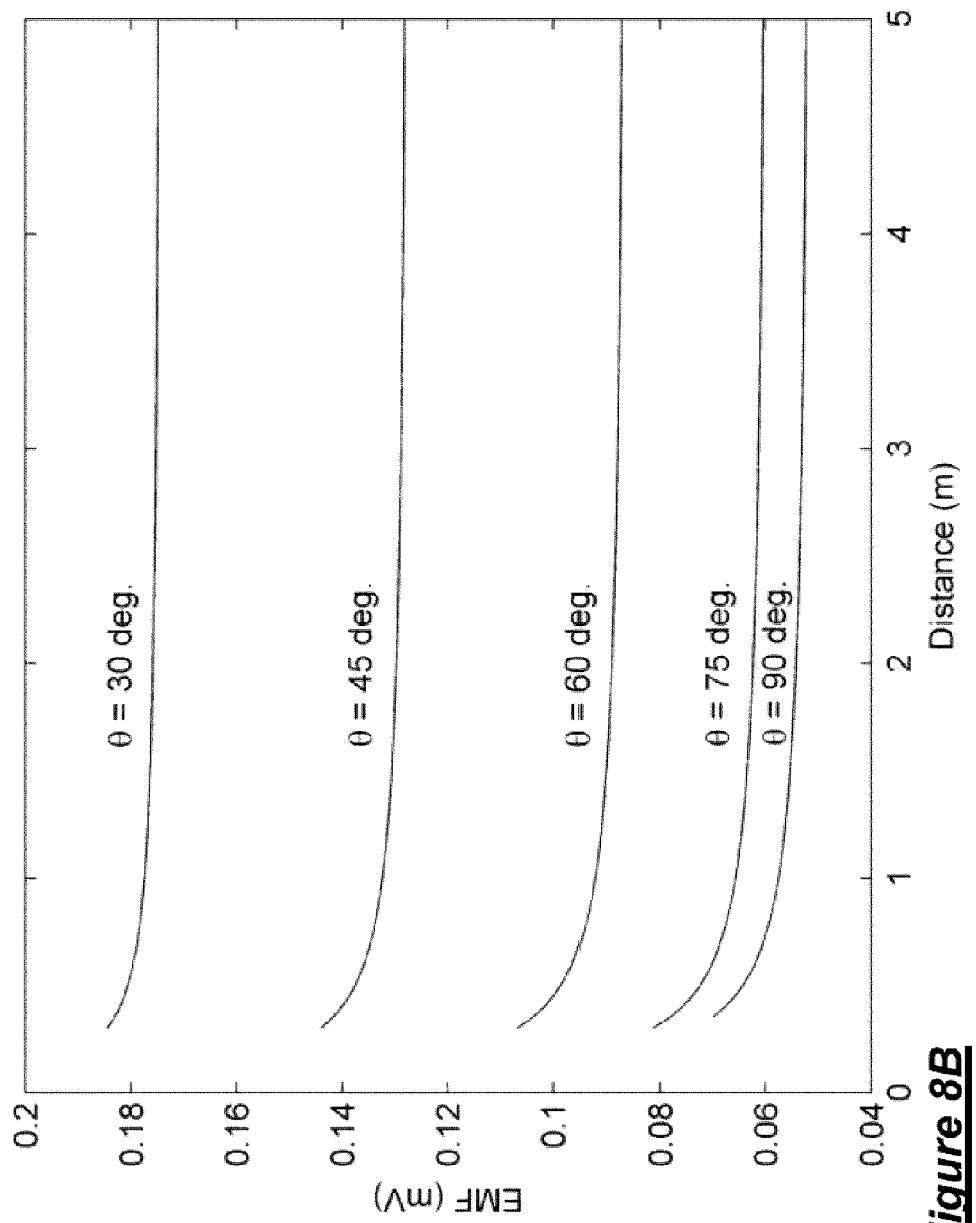
FIG. 8B is a schematic plot illustrating the variation in the EMF as a function of object distance for different azimuthal angles in accordance with the proposed solution.

An optimized EMF signal is needed for pulse durations in the nanosecond range. For a nanosecond pulse a $\Delta I/\Delta t$ can be in the order of 10,000 amps/s. The duration and amplitude of such short pulses selected such that the resulting magnetic flux is sufficient to be measured in the coil of the neighboring eye, while being insufficient to stimulate nearby nerves so as to trigger nerve activity. Very short pulses of the order of a nanosecond can be discriminated over background noise, and synchronization or phase locking the generation and detection of the pulses is not required. Using the generalized mutual inductance relation presented above with d=6 cm, R=12.5 mm, b=5 mm, and N=20 turns, the variation of the EMF signal at different values of azimuthal angle $\theta$ as a function of target distance L is presented in FIG. 8B. The induced EMF in the detecting coil varies much more with the azimuthal angle $\theta$ than with distance L at large target distances. There is still an ambiguity at target distances L less than 50 cm where a single EMF value can imply two different azimuthal angles $\theta$ but the azimuthal angle $\theta$ values will be within a close range (on neighboring curves) leading to corresponding distances L of the same order. A table of the full range of EMF values as a function of azimuthal angle $\theta$ can be sufficient to provide an estimate of the azimuthal angle $\theta$ (for example such a table can be provided by calibration) but may not carry enough information to find a target distance L for comfortable viewing with best focus (although in an ocular implant this can be a great improvement from a removed natural lens suffering from presbyopia and/or cataract).

However, it is noted that the EMF curves have a slope varying strongly with distance L at close target object distances. As mentioned hereinabove, the eyes do not sit still even when fixed on a stationary target object. The eyes move randomly in a microsaccades motion. In accordance with an implementation of the proposed solution, the differential microsaccades motion $\Delta\theta$ between the eyes is relied upon to provide an angular jitter to detect changes in EMF from repeated EMF measurements at the detecting coil.

Figure 8C:
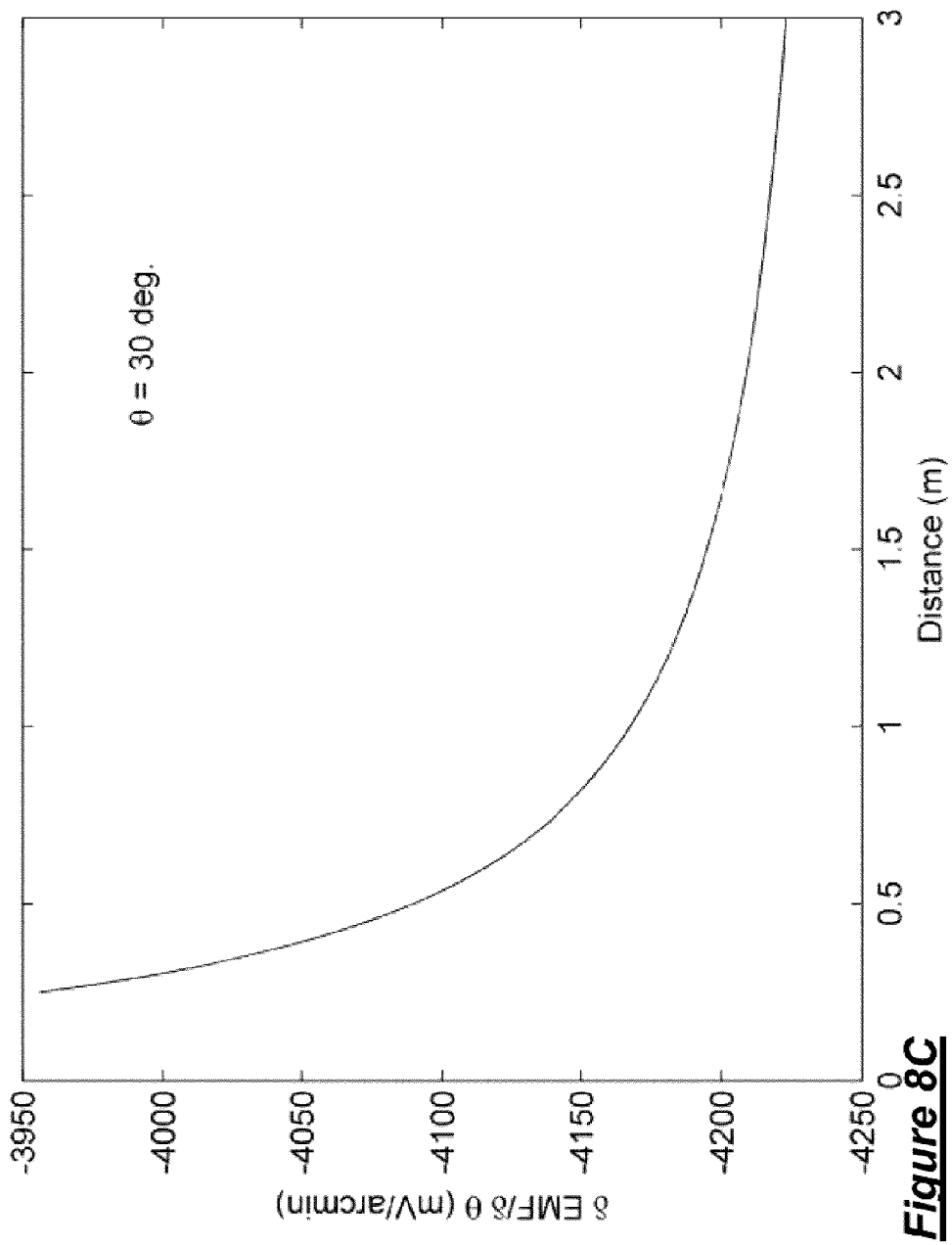
FIG. 8C is a schematic plot illustrating the variation of the slope of EMF as a function of object distance for an azimuthal angle in accordance with the proposed solution.

The variation in EMF caused by eye jitter is given by:

$$\Delta EMF = \frac{d}{d\theta} EMF \cdot \Delta\theta, \qquad \text{Eq. 8}$$

where $\Delta\theta$ is the microsaccade amplitude (2 to 120 arc-min.). The EMF derivative relative to $\theta$ (in mV/arcmin.) is illustrated in FIG. 8C for an azimuthal angle of 30 deg. It can be seen that the EMF variation caused by the eye jitter has a strong dependency on the target distance L at close target object distances. With knowledge of the azimuthal angle $\theta$, even if approximate as described herein above, more accurate target distance L can be obtained.

In some implementations, two pieces of information can be used, an average of multiple EMF measured values over a time period longer than microsaccades jitter (30 Hz to 70 Hz) and the EMF variation (spread) caused by the microsaccade, to derive the target distance L from the calibration table. The spread of EMF measured values will be small for far target object distances L and large for near target object distances L. Incidentally, individual eye distances to the target can be calculated from the target distance L and the azimuthal angle $\theta$ via the above toe-in angle relationships.

Figure 8D:
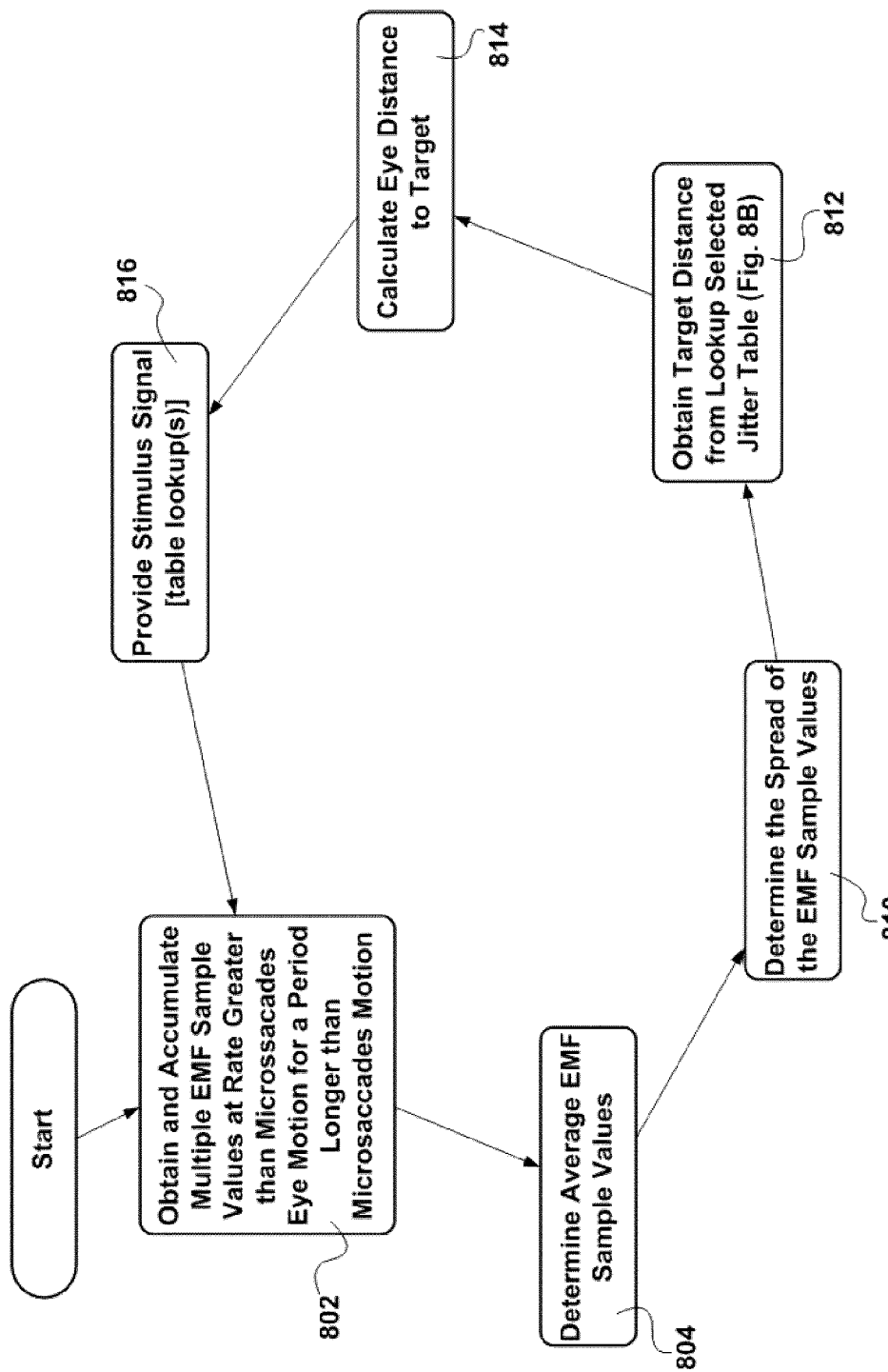
FIG. 8D is a schematic diagram illustrating a process for obtaining a target distance L and an azimuthal angle θ in accordance with the proposed solution.

FIG. 8D illustrates a process for obtaining the target distance L and the azimuthal angle $\theta$ in accordance with an implementation of the proposed solution. The process starts at 802 by obtaining and accumulating multiple EMF sample values at a rate greater than microsaccades eye motion (for example >70 Hz) for a period longer than microsaccades motion (for example >1/30 Hz). It is understood that if $\Delta I/\Delta t$ pings are transmitted by the other ocular prosthesis, an appropriate high frequency pass filter and triggering components are employed, see FIG. 2D. If a signal having a frequency is transmitted by the other ocular prosthesis, than step 802 obtains multiple EMF sample values at a rate faster than the signal frequency over at least a few cycles (FIG. 2D).

An average of the accumulated EMF sample values is determined 804. A spread in measured EMF values is obtained 810 from the accumulated EMF sample values. The spread can be simply the minimum and maximum values of the set of samples, or it can be the result of a more complex analysis of the set of accumulated samples. A table lookup in the EMF variance table is performed 812 based on the obtained average EMF and the obtained spread in EMF values to obtain the target distance L, and if desired, the azimuthal target angle $\theta$. The table can essentially contain the information of FIG. 8B, namely for each given average EMF values, the spread value, indicative of the slope, allows for distance to be determined. It is understood that table entries may not be available for every average EMF value due to sparse calibration, and that table entries can be interpolated. However, if the target distance L is large (essentially infinity, larger than a threshold) the interpolation step can be omitted despite sparse calibration.

Having obtained the target distance L, an individual distance from the eye to the target can be calculated 814 based on the eye-to-eye distance d and the eye radius R. However, if the target distance L is large (essentially infinity) calculation of individual eye target distances can be omitted.

A stimulus signal is obtained 816, for example through at least one table lookup, from the target distance L for provision to the electric field driver 1310. The process resumes from 802.

Once a prosthesis has determined the distance or optical power parameter, it can, optionally, share that information with the other prosthesis, for example by using data communication through the coils (Rx/Tx in FIG. 2D). The other prosthesis can use the information directly for control (without otherwise determining the distance), or it can compare the information to what it independently determined for confirmation or calibration purposes.

From an implementation perspective, signal processing also requires consideration. Noise aspects are considered first. The magnetic fields generated by the human brain are in the range of ~50-500 fT @<100 Hz while environmental magnetic noise will be 5 to 6 orders of magnitude greater (Hämäläinen, M. et al., "Magnetoencephalography—Theory, Instrumentation, and Applications to Noninvasive Studies of the Working Human Brain," Rev. Mod. Phys. 65, 413, 1993, which is incorporated herein by reference). As a comparison, the magnetic field produced by one of the coils via pings in the above proposed system can be in the range of ~70 pT at the position of the second detecting coil for typical values of N=20 and $\Delta I$=100 µA. This value is much higher than the magnetic field generated by the human brain, but less than environmental noise. However, the environment noise will be incoherent at lower frequencies compared to the convergence signal employed in the proposed system at small $\Delta t$ (short pings). For certainty, the magnetic flux resulting from the transmitted convergence signal is insufficient to induce sufficient currents in surrounding nerves so as to stimulate nerve activity, while being sufficient to be measured in the coil of the neighboring eye. The detection of the signal could be optimized by synchronizing the detection scheme to the convergence signal emitted by the neighboring coil. For example this can be implemented by employing a phase locked loop amplifier in the detection electronics associated with the detecting coil for transmitted signals having a frequency (FIG. 2D), or by employing a high band pass filter and trigger for transmitted pings (FIG. 2D).

Figure 9:
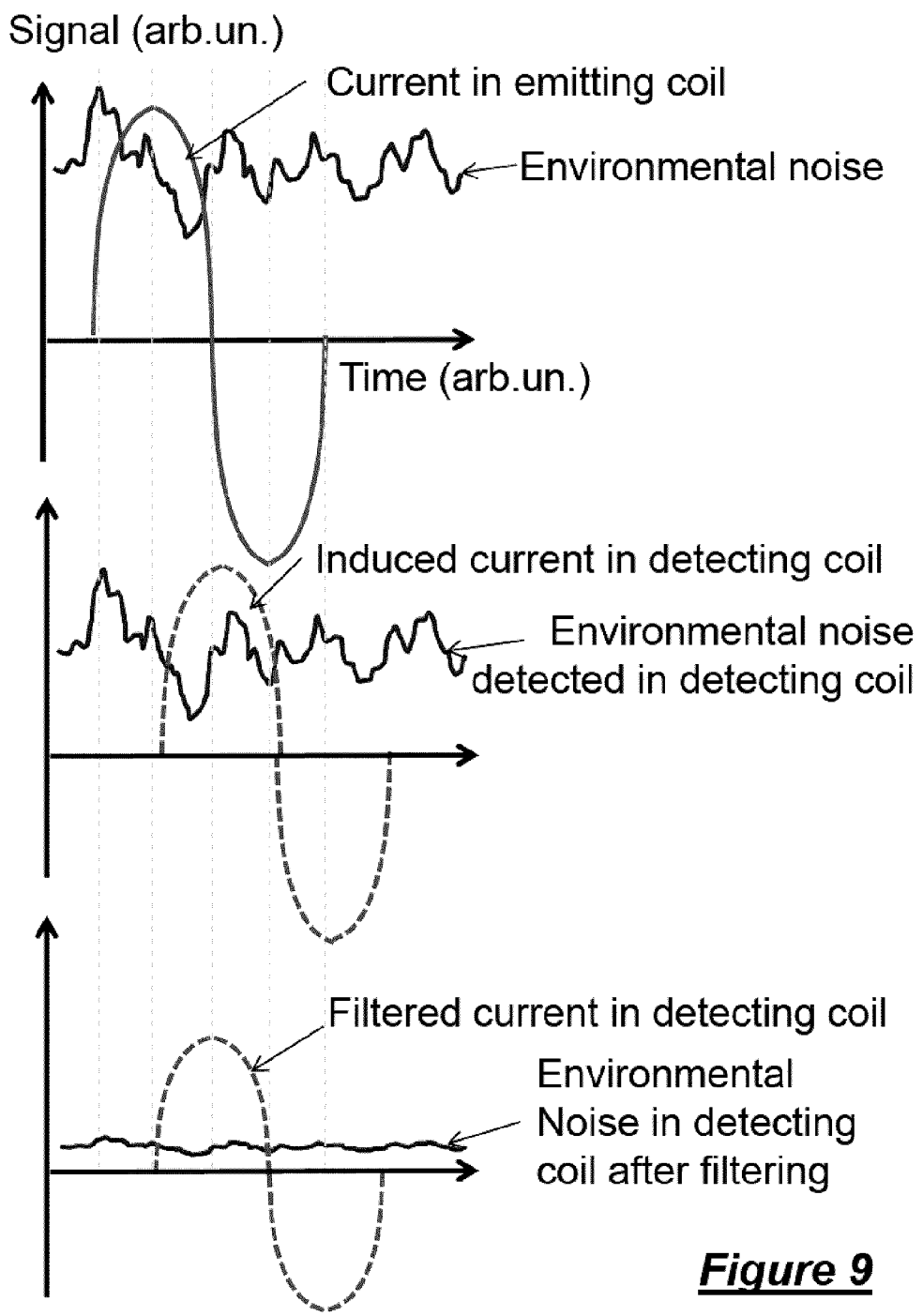
FIG. 9 schematically illustrates mutual coupling by sinusoidal signal firing in the presence of noise in accordance with the proposed solution.
Figure 10:
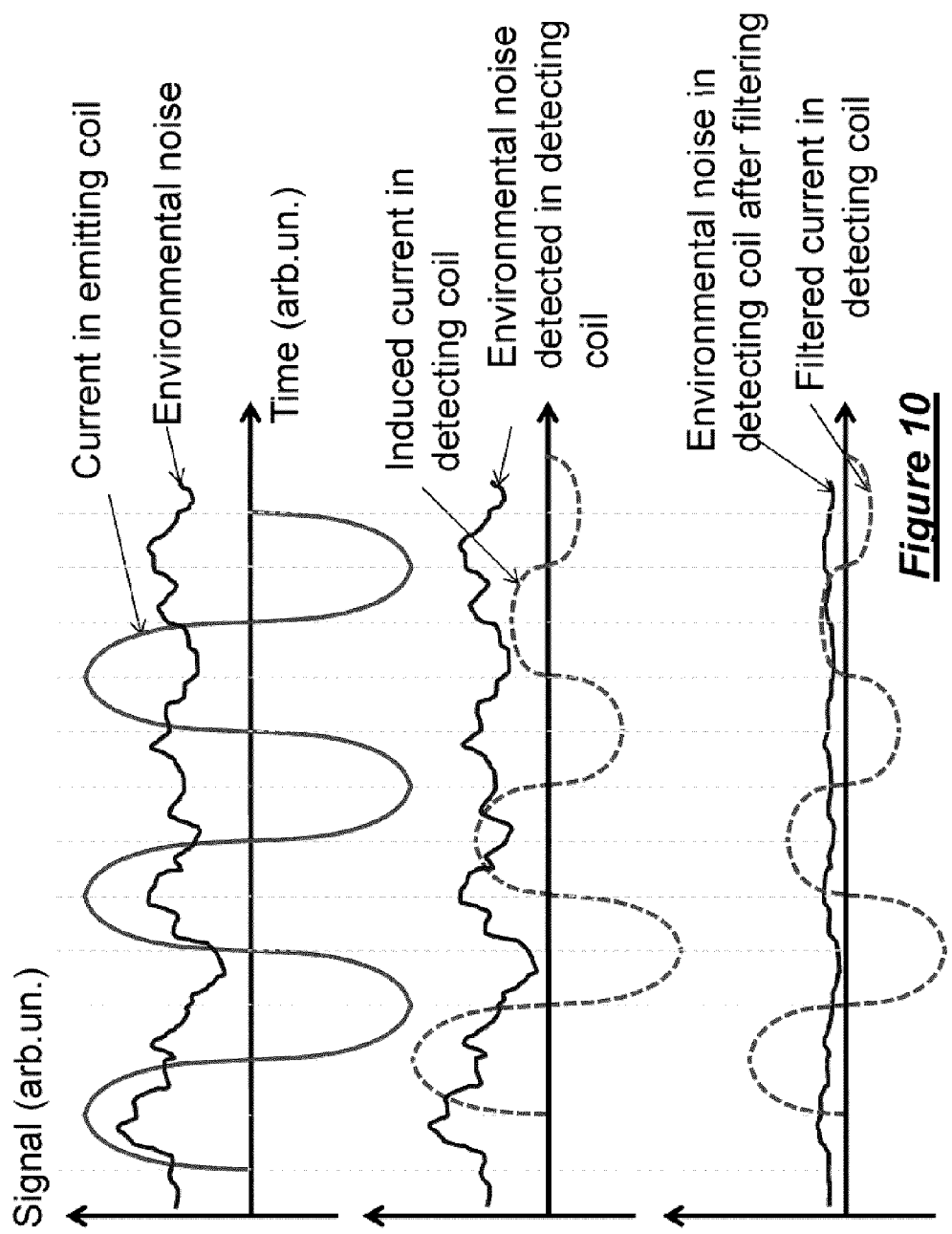
FIG. 10 schematically illustrates the dynamic mutual coupling by sinusoidal signal firing in the presence of noise in accordance with the proposed solution.

In accordance with one implementation, a process of noise filtering is schematically illustrated in FIG. 9 for a constant signal signifying no change of accommodation being required. FIG. 10 schematically illustrates the signal filtering process and the inductive coupling, but with time changing convergence signal between the two eyes according to the desire of the patient to accommodate, which, in turn, generates a corresponding change of mutual inductance as an electrical signal for accommodation. For example the envelope of the received signal diminishes with time.

Figure 11:
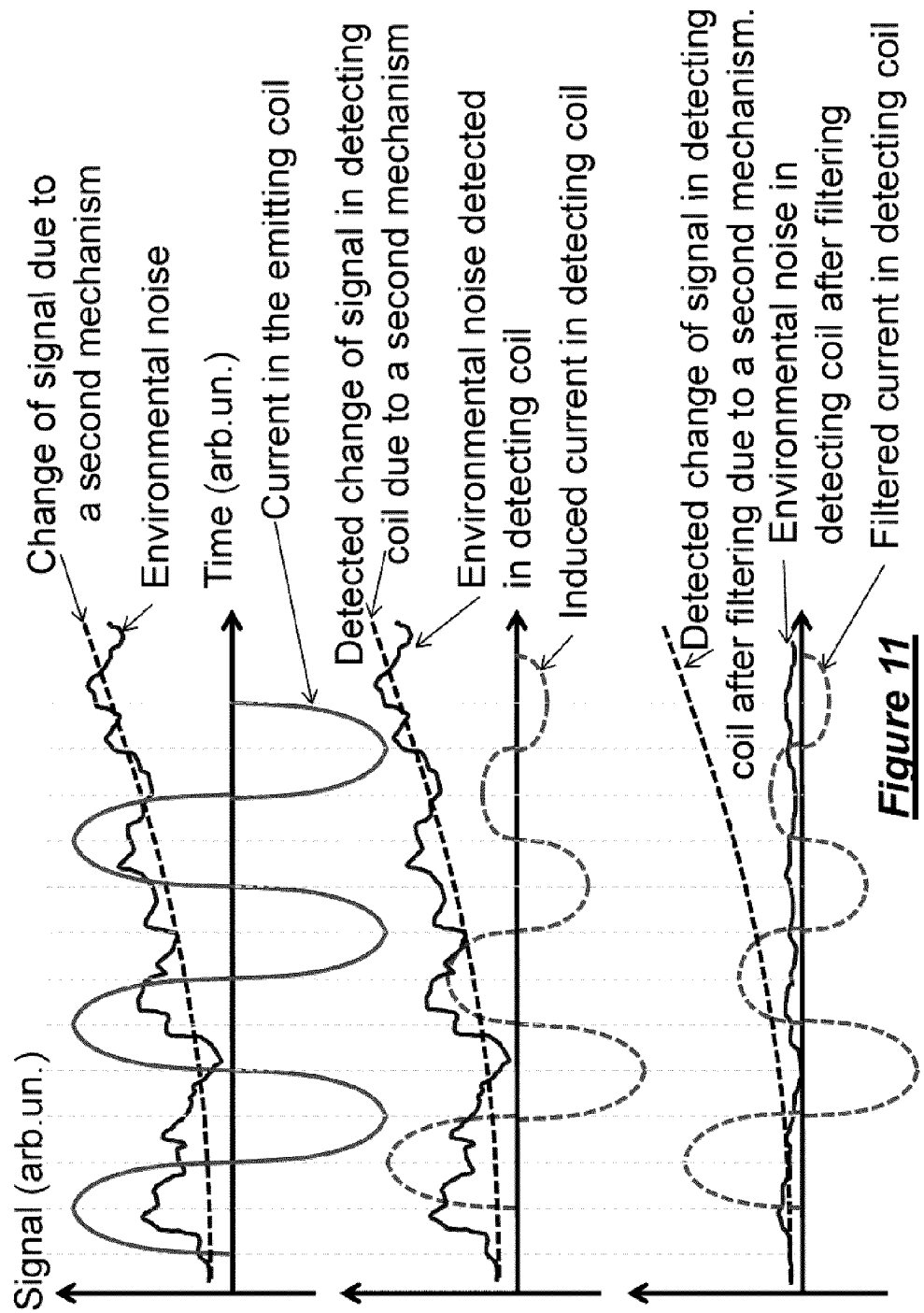
FIG. 11 schematically illustrates the dynamic mutual coupling by sinusoidal signal firing in the presence of noise and a second accommodation signal in accordance with the proposed solution.

In accordance with another implementation, FIG. 11 schematically illustrates a signal filtering process during the inductive generation of a signal composed of mutual coupling, environmental noise and another accommodative signal, coming for example from muscular activity. The spectral-temporal characteristics of this last convergence signal can be quite different. Signal analysis during the training process can be employed to define signal characteristics and pre-program the signal processing algorithm to use this as a second source of definition of the accommodative signal. As such, the fidelity of accommodation obtained by the prosthesis can be improved.

In accordance with another implementation, as the brain exhibits the same magnetic permeability as air, the performance could also be improved by adding a material (such as magnetic or ferromagnetic elements) having a high magnetic permeability around the coils or in close proximity to the eyes to increase (concentrate) the magnetic field produced.

When ping signal impulses are generated by the transmit coil, the generated electromagnetic signal will have additional frequency components due to the above mentioned saccades, microsaccades and other patient specific dynamic fluctuations. The analysis of the spectral signature of the detected electromagnetic signal in the detecting coil, during various trials of accommodation, can provide important information to minimize the error of accommodative signal generation/detection. Thus, in another embodiment of the proposed solution, the above mentioned signature is identified experimentally after the ocular prosthetic system is worn or implanted and has achieved stable operational state (and after patient's eyes have stabilized). A correspondence table can be established where the spectral signature of the signal is associated to (put in correspondence with) different desired steps of the patient vision accommodation. This table can then be used to filter the detected signal and to generate (816) the desired accommodation signal.

In other implementations, the above mentioned correspondence table can be self-generated during the operational life of the ocular prosthetic system. The convergence and stabilization process of the accommodative effort can be used as criteria for the establishment of the correspondence table. The corresponding algorithm can start by emitting a standard set of electrical signals from the emitting coil and by the detection of the combined (complex) signal at the detection coil of the other prosthesis. The spectral (amplitude, frequency, time, etc.) signature of the detected signals can be continuously identified and recorded in a short term memory storage until the establishment (stabilization) of a trial accommodative signal and a corresponding variation of the optical power of the vision prosthesis. In the case of successful accommodation, this establishment of the signal can be considered successful accommodation. If the patient is not satisfied by the generated optical power change, then the patient's accommodative effort is continued and the corresponding signals are detected and compared to a (standard) pre-programmed table and the correspondence table is consequently modified.

Interprosthesis Communications

In accordance with another embodiment of the proposed solution, FIG. 2C illustrates communications between two (implanted or worn) ocular TLCL prostheses. Each ocular prosthesis also has a modulator/demodulator configured transmit a signal pattern discernible by the other ocular prosthesis. For example, the IOL controller 1330 illustrated in FIG. 2D employs window timing information provided by the PPL amplifier and modulator/demodulator (Rx/TX) block to drive the coil 1320. In this manner a parameter, for example an ambient sensor value detected by one prosthesis is conveyed to the other intraocular prosthesis for comparison, reinforcement, reuse, etc. In one implementation, the signal pattern is encoded over the convergence signal employed as a carrier.

USE EXAMPLE

In use, an optometrist can employ different techniques to perform at least one vision quality measurement (FIG. 2A) for example such as, but not limited to, using a refractometer to determine low order aberrations of the eye. For certainty, performing such a vision quality measurement can be automated, wherein human interaction can be limited to initiating the vision quality measurement at the appropriate time.

Using a refractometer on the natural eye lens provides information about the physiology of the overall eye with the intent to determine low order aberrations such as, but not limited to, a predominant optical power required for comfortable vision at infinity. Based on the low order aberration information, for example an intraocular TLC lens prosthesis can be selected, possibly including a base optical power based on a combination of the index of refraction and curvature of the lenticular body(ies) 1308 for example illustrated in FIG. 1A or 12, possibly also including a fixed optical power element 1304 for example as illustrated in FIGS. 13 and/or 14. Alternatively, a contact lens prosthesis can be selected in similar fashion. The intent of the selection is to provide comfortable unaided vision employing the ocular prosthesis in an unpowered state, for example comfortable far vision, comfortable vision at an arm's length or comfortable vision at a reading distance which can depend on the TLCL employed and the patient's preference. As an example, the TLCL geometry can be manufactured to employ fixed optical power for a 20-20 vision eye prior to cataract surgery (FIGS. 13/14). The selection of the TLCL intraocular prosthesis can also take into account expected capsular bag deformation in the absence of the natural lens.

Next, in the case of the contact lens, the contact lens prosthesis is worn. In the case of the intraocular prosthesis, the ophthalmologist surgically implants the TLCL intraocular prosthesis, using methods beyond the scope of the present description. Preferably the TLCL intraocular prosthesis is rolled or folded for insertion into the capsular bag through a small incision and allowed, or caused, to unfurl within the capsular bag. If the intraocular prosthesis is configured to also have a fixed optical element 1304 which compensates for base coma and astigmatism, the ophthalmologist would need to correctly orient (rotate) the prosthesis. A surgical refractometer, or other suitable optical equipment, can be employed for the purpose. The intraocular TLCL prosthesis is to be registered with respect to the eye's optical axis irrespective of the correct rotational orientation mentioned as best as possible.

Using an external ocular lens prosthesis programming module (FIG. 2A), the ocular prosthesis is configured to correct visual aberrations of the eye. This can include programming an optical transfer function including voltages, frequencies and phase differences for the TLCL ocular prosthesis to provide the corrective wavefront correction. For example, the programming at least provides a bias in terms of an RMS voltage, a frequency or a phase angle difference. The IOL controller 1330, as illustrated in FIG. 2D, employs the modulator/demodulator block (Rx/Tx) and coil 1320 to provide a physical programming interface.

The patient is instructed to observe a target object at infinity while each ocular prosthesis is instructed to characterize the convergence signal transmitted by the other intraocular prosthesis as the zero toe-in/zero convergence signal. Characterization of the convergence signal at other distances and angle(s) in the field of view of the patient can be performed by instructing the patient to focus on a appropriately positioned object/card and instructing the prostheses to characterize the convergence signal. The angles include an azimuthal angle. The characterization can be stored in lookup tables using the distance and angle(s) as indices, for example as described hereinabove.

Large vision variation can be experienced during the first month as the eye (heals and) gets used to the new norm. A post surgery period is allowed for the eye to heal, seal the incision and allow the tissues of the eye to settle by which it is understood that the quasi-final eye pressure and corneal tension is being exerted. In the case of the contact lens, a period of continued wear is allowed to pass. The tissues of the eye are subject to tissue plasticity, as are the muscles of the eye which in the intraocular implant case may have less of an effect on the prosthesis and therefore on the overall vision post surgery. Some muscle fibers may atrophy.

Depending on the indicated vision recovery regimen, one or more re-programming of the TLCL intraocular prosthesis can be performed. At the same time the convergence signal may be recharacterized. In accordance with a use example, a patient vision quality measurement is performed (FIG. 2A) for example employing Shack-Hartmann aberrometry, or a suitable vision field test, which can provide the post operative optical transfer function of the TLCL intraocular prosthesis aided eye. For certainty, the vision quality measurement can be automated without human intervention beyond initiating the vision field test at the appropriate time. The post operative optical transfer function of the aided eye can be compared (FIG. 2A) with an ideal optical transfer function and differences determined. The comparison and determination, via associated calculations (FIG. 2A), provides for example one of a drive signal bias parameter, a drive signal phase difference or an entire optical transfer function. The ophthalmology professional can then reprogram the TLCL intraocular prosthesis either by loading an entire optical transfer function via the remote programming interface or individual programming parameters of the TLCL intraocular prosthesis can be adjusted without removing or replacing the TLCL intraocular prosthesis. For certainty, such reprogramming can be automated without requiring human intervention beyond initiating reprogramming. Reprogramming is only limited by the performance limits of the TLCL ocular prosthesis and the prescribed eye vision correcting regimen. Spare ranges in operational parameters (for example spare optical power) can increase such performance limits. For certainty, eye vision recovery/correction regimens are beyond the scope of the present description and described elsewhere.

The long term state of the intraocular prosthesis implanted eye or of the contact lens wearing eye includes a slow aging process past about a month. After the first few months, the TLCL ocular prosthesis can be further reprogrammed to account for aging effects of the eye. Preferably, in the case of the TLCL intraocular prosthesis the reprogramming is performed without removing or replacing the TLCL intraocular prosthesis.

Implementations of Intraocular TLCL Prostheses

Suitable biocompatible/non-toxic materials have been tested and are assumed in the following. Thermal cycling tests confirm long term storage and have shown compatibility with sterilization requirements while retaining operability. Experimental tests have shown long life times measured in years. It will be appreciated that TLCL ocular optical devices can be fabricated using layer-by-layer assembly and, preferentially, in a parallel way (many units simultaneously, called "wafer level"). While TLCLs configured in accordance with the above description exceed the required operational parameters of an intraocular TLCL prosthesis, it will be appreciated that miniaturization and low power operability of such TLCLs in an adaptive intraocular prosthesis is subject to greatly varying dimensions depending on geometry, choice of materials, and particularly depending on tradeoffs between operational parameters. Operation within possible operational parameter(s) range(s) may be sacrificed in providing a TLCL ocular prosthesis.

The typical available capsular bag size following natural lens removal is about 9 mm in diameter and 4 mm in thickness/depth (anterior to posterior dimension). The diameter 350 of a hole-patterned electrode aperture is referred to herein as a clear aperture of the TLCL. A smaller diameter 360 represents an accommodative clear aperture (of the TLCL) and includes a region which refracts incident light at an optical power. For example, TLCLs having an accommodative clear aperture 360 of about 4.5 mm can provide at least 1.7 diopters employing a single TLCL, at least 3.5 diopters employing a dual TLCL, and at least 7 diopters employing a bipolar TLCL. A 4.5 mm accommodative clear aperture 360 benefits from relatively small incisions. Larger accommodative clear apertures 360 while permitting operation in lower light conditions would require larger incisions and/or a foldable TLCL structure however at reduced optical power. For example a 6 mm accommodative clear aperture 360 would provide roughly half the optical power of a TLCL having 4.5 mm accommodative clear aperture 360. Even at 6 mm accommodative clear aperture, sufficient structural material reserve around the clear aperture 350 can be provided to ensure operability without violating capsular bag dimensions. Conversely, smaller accommodative clear apertures 360 benefit from requiring smaller incisions and operation at higher optical powers providing greater coverage of the juvenile accommodation range. For example, TLCLs having an accommodative clear aperture 360 of about 3 mm can provide at least 3.5 diopters employing a single TLCL, at least 7 diopters employing a dual TLCL, and at least 14 diopters employing a bipolar TLCL. Smaller accommodative clear apertures 360 while providing increased optical power can restrict light throughput. Light throughput can be increased by expanding light transmittance of the TLCL structure layers and/or that of any encapsulating material. For example, employing more flexible thinner single TLCL or single bipolar TLCL allows at least 90% transmittance. Less flexible thicker dual TLCL allows at least 80% transmittance. Reducing the thickness of some layers can change transmittance depending on material/physical properties of the layer material.

Assuming 20-20 vision prior to removal of a natural lens for example during a cataract operation in an adult, an optical power range of 3 diopters, while limited compared to the juvenile accommodation range, typically can provide sufficient optical power variability to permit a focus range spanning from infinity to about 30 cm. An optical power range greater than 3 diopters can provide closer focus and/or increased ability to correct imperfect vision. For example, 2.5 diopters can be useful for correcting presbyopia. Different adaptive accommodation is required depending the visual condition which is to be addressed and therefore different optical range variability is employed.

For example, the (dual) TLCL structure can be configured to focus at infinity employing maximum optical power and at a closest focusing distance employing minimum optical power. Depending on whether the TLCL is configured as a positive lens or a negative lens, infinity focus or closest focus can correspond to maximum power drive or minimum power drive. The configuration may depend on factors such as focusing ability of the eye prior to surgery, selected mode of driving the TLCL, etc. Alternatively, without limiting the invention, employing a bipolar TLCL infinity focus can be provided by driving the TLCL at maximum optical power of one polarity, closest focus can be provided by driving the TLCL at maximum optical power of the other polarity, and focus at a working/reading distance/arm's length can be provided employing zero optical power adjustment.

The TLCL substrates can include a degree of flexibility permitting the TLCL to bend and thus an incision of reduced size. The above assumes 100 μm thick glass substrates. Greater flexibility can be achieved in (dual) TLCL structures by eliminating one of the substrates, or by employing thinner substrates. Substrates can be as thin as 50 μm which combined with compliant (pliable) adhesives can provide a useful amount of flexibility and reduce incision size. Alternatively, incision size can be further reduced by employing a TLCL having a circular outer shape. While typical TLCLs are wafer level manufactured and singulated employing standard scribe and dicing techniques into individual squares, laser cutting techniques have been successfully tested to singulate circular intraocular TLCLs.

The (dual) TLCL structure can be encapsulated in a lenticular body 1308 which represents an intraocular/contact lens prosthesis. A lenticular body 1308 of a substantially spheroidal outer shape can be employed as illustrated in FIG. 12. It is appreciated that the natural lens and capsular bag are not necessarily symmetric.

Alternatively, if the natural eye prior to natural lens removal is not 20-20, then a baseline correction can be provided by employing a combination of a lenticular body 1308 shape configured to have a composition and an index of refraction. FIGS. 13 and 14 illustrate encapsulated TLCLs having additional fixed optical power lens elements 1304 (non-tunable) deposited thereon. Either or both flat surfaces the TLCL can have a fixed optical element 1304 deposited thereon. A combination of the lenticular body 1308 and fixed optical power elements 1304 can be employed to shift or amplify the accommodation range of the intraocular prosthesis. For example, if the fixed optical element 1304 provides +11 diopters and if the TLCL provides an accommodation of 7 diopters (positive TLCL), then the optical power provided by such an intraocular TLCL prosthesis can change from 11 to 18 diopters. If a negative TLCL provides −7 diopters of accommodation, then the optical power provided by such an intraocular TLCL prosthesis can change from 11 to 4 diopters.

Figure 1B:
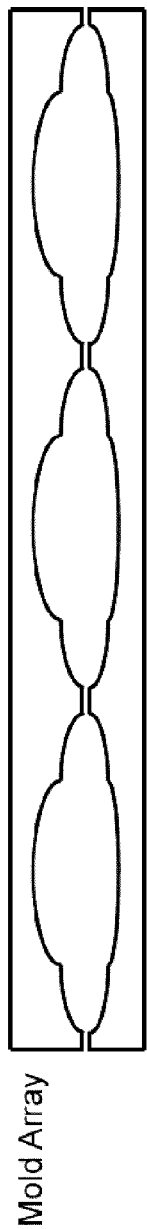
FIG. 1B is a schematic diagram illustrating a cross-section through a mold array for manufacturing encapsulated tunable liquid crystal lens intraocular prostheses in parallel in accordance with the proposed solution.

In accordance with some embodiments of the proposed solution, an integral ocular prosthesis includes the TLCL 1302, an electronics package 1300, and power storage on a flexible Printed Circuit Board (PCB), for example made of (biocompatible) Kapton™ (Kapton is a trademark of E. I. du Pont de Nemours and Company or its affiliates), the flexible PCB itself having an aperture. An example of such an integral intraocular prosthesis is illustrated in FIG. 1A to include encapsulating material forming a pronounced fixed optical power element (1304) over the TLCL 1302 and also encapsulating the electronics package 1300, and power storage component(s). It is understood that FIG. 1A is highly schematic, the lobed shape provides high optical power fixed optical lens elements 1304 by employing pronounced lenticular shapes. FIG. 10 illustrates a top view of integral intraocular prosthesis showing the power source and electronics package 1300 being disposed around the periphery of the intraocular prosthesis. The FIG. 1B illustrates a cross-sectional view of a mold for encapsulation during manufacturing of an array of intraocular TLCL prostheses. The mold includes an array of reservoirs for holding encapsulating material.

With the (coil) sensor being disposed around the periphery of the intraocular TLCL implant, such an internal pressure sensor can be configured to detect external mechanical action exerted onto the capsular bag, for example by the ciliary muscle.

Alternatively, an external deflection sensor and transmitter are illustrated in FIG. 1A, external deflection sensor and transmitter which can be affixed to a muscle, not limited to the ciliary muscle, to measure physiological change in the form of muscle action and to transmit a stimulus signal to a pickup coil in the intraocular prosthesis. Muscles of the eyelid are other examples. Eyelid muscles have the advantage that they can be consciously controlled besides being autonomously/instinctively controlled by the body. For example the deflection sensor can include a piezo element. A number of piezo element arrangements can be configured to react to muscular bend, contraction, etc. to provide a feedback stimulus signal. Such piezo elements are compatible with any muscular environment in the vicinity of the eye including facial muscles about 1 cm away from the eye.

For certainty, external physiological change measurements do not necessarily have to be transmitted. FIGS. 15A, 15B 16A and 16B (not anatomical) schematically illustrate integral intraocular prostheses detecting physiological changes outside the eye. Advantages are derived from an integral ocular prosthetic device.

Figures 15A, 15B:
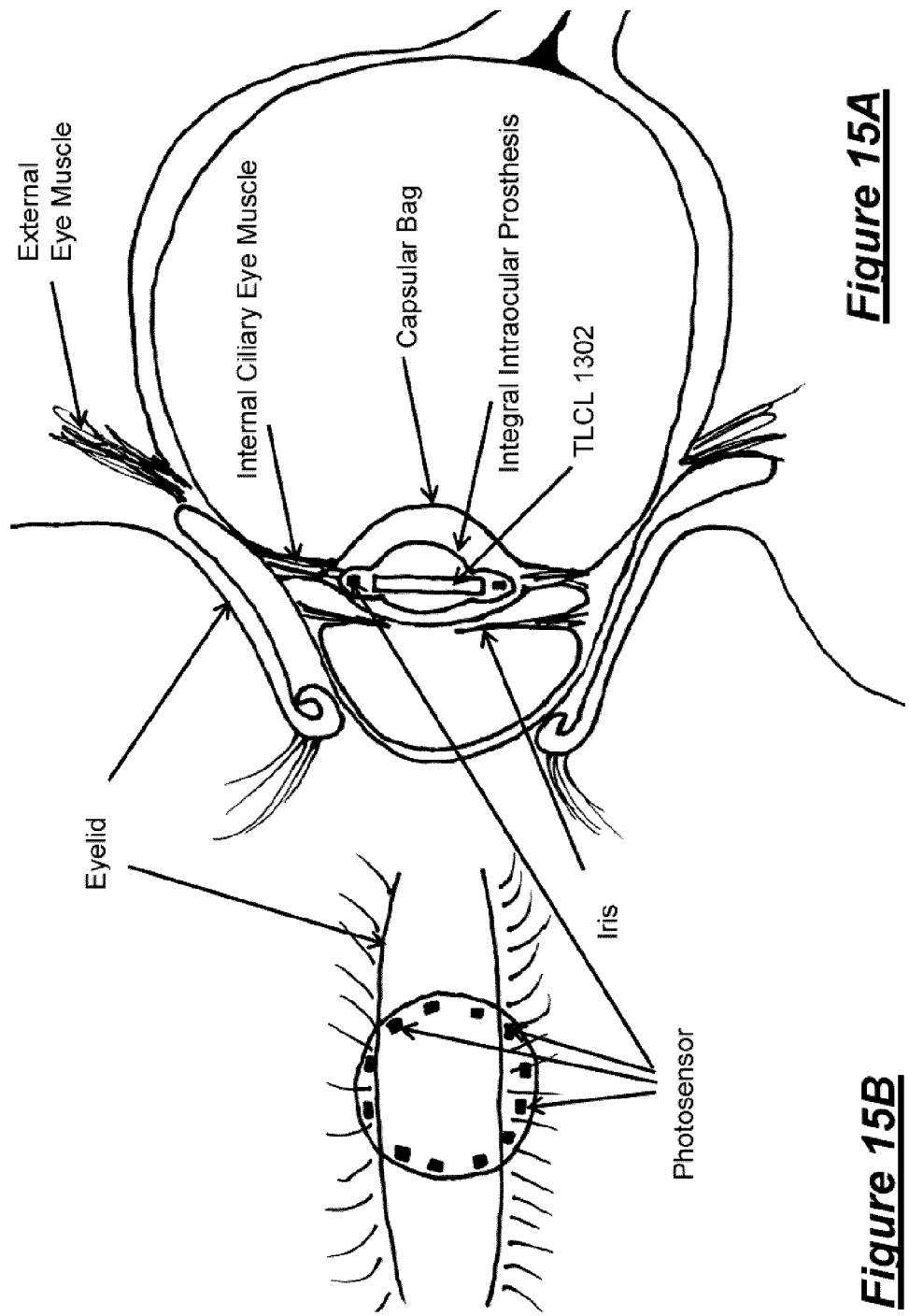
FIGS. 15A and 15B are schematic diagrams illustrating an integral intraocular prosthesis detecting physiological changes outside an eye.

In accordance with one implementation of the proposed solution, ambient sensor 1320 includes at least one, typically a number of photosensors disposed around the TLCL for detecting the position of the eyelid(s). FIG. 15A illustrates the location of the photosensors, the inset FIG. 15B illustrates an example of a photosensor distribution around the integral intraocular TLCL prosthesis. The greater the accommodative clear aperture 360 employed, the more the photosensors spend time behind the iris for an intraocular TLCL prosthesis implanted in the capsular bag. The inset FIG. 15B illustrates the relative position of the eyelid with respect to the photosensors during a blink or squint. A blink can be differentiated from a squint for example by low rate sampling which statistically misses a blink or by a relatively long term integration of light falling onto the photosensors. The position of the eyelid can be inferred from the pattern of light measurements. It can be appreciated that no additional procedure, aside from that replacing the natural eye lens with the integral intraocular TLCL prosthesis, is necessary in employing this implementation.

Figures 16A, 16B:
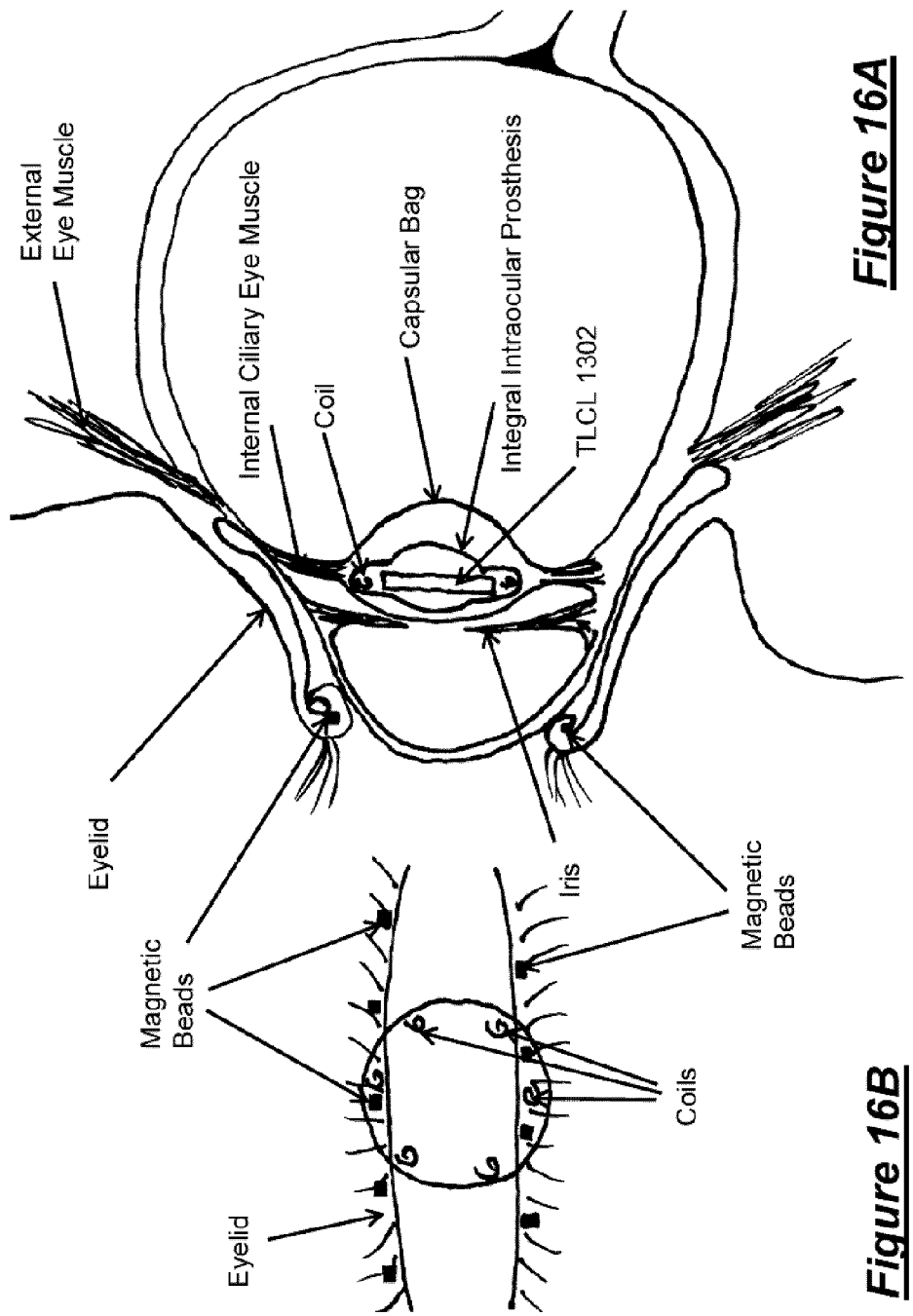
FIGS. 16A and 16B are schematic diagrams illustrating another integral intraocular prosthesis detecting physiological changes outside an eye.

In accordance with another implementation of the proposed solution, the physiological change sensor includes at least one coil, typically a number of coils sensitive to varying magnetic fields. At least one magnetic bead, typically a number of magnetic beads, for example including niobium, each encapsulated in a biocompatible material, can be implanted for example via injection into the rim of the eyelid as schematically illustrated in FIG. 16A. The human eye does not sit still moving involuntarily in random directions at a frequency range 30 to 70 times per second in microsaccade motion. The coil(s) can pick up magnetic field variations induced by both eyelid action and microsaccade involuntary eye movement, and determine the degree of closure of the eyelid which can then be provided as a stimulus signal. Employing a number of magnetic beads the orientation of the eye within the eye socket can be ascertained. Dual intraocular prostheses can share eye orientation information, for example to determine focusing distance from angle of view measurements as described hereinabove.

Functional Ocular Prosthesis

It is noted that the TLCL 1302 appears in an electrical circuit as a capacitive load. For example, at 7V/10 kHz operation, a TLCL having a 3.0 mm accommodative clear aperture 360 has a typical capacitance of about 70 pF, while a dual TLCL having a 4.5 mm accommodative clear aperture 360 has a typical capacitance of about 320 pF. Lower voltage operation is possible, however fast optical power transition times favor high voltage operation. For example, 7V operation can provide optical power transition times of about 0.4 s but can vary between 0.2 s and 0.6 s.

Figure 18:
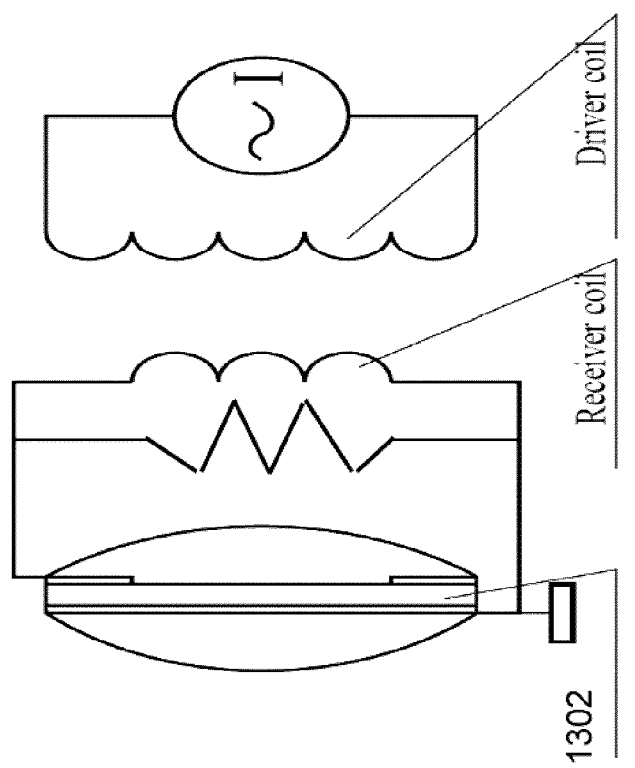
FIG. 18 illustrates wireless inductive drive in accordance with the proposed solution.
Figure 19:
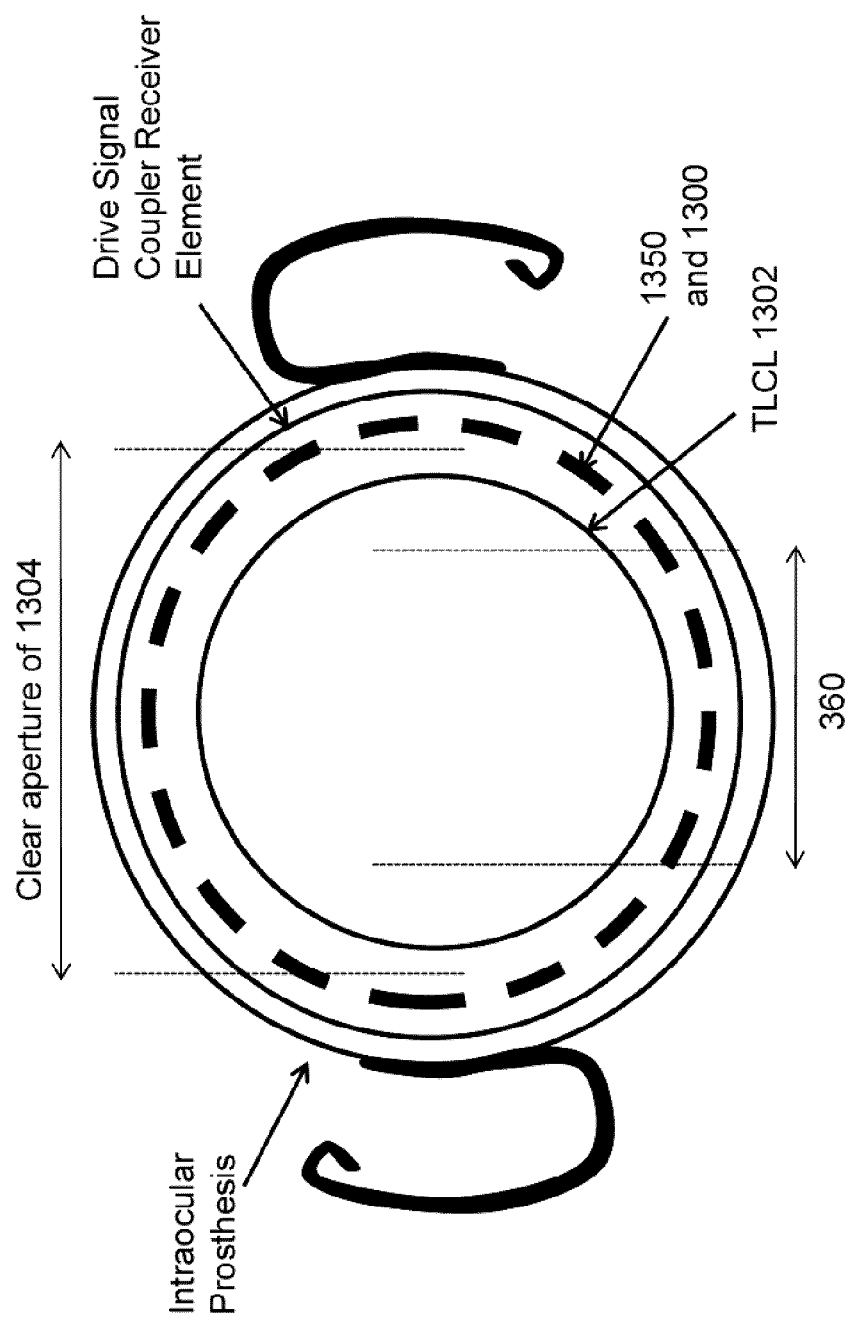
FIG. 19 is a schematic diagram illustrating the location of a drive signal receiver element of a drive signal coupler in accordance with the proposed solution, wherein similar features bear similar labels throughout the drawings. Reference to "top" and "bottom" qualifiers in the present specification is made solely with reference to the orientation of the drawings as presented in the application and do not imply any absolute spatial orientation.

FIG. 18 illustrates an example of wireless TLCL drive employing a drive signal coupler. FIG. 18 illustrates inductive drive coupling employed with the TLCL 1302 connected as a capacitor in an LRC resonant circuit. It is understood that FIG. 18 is an electronic schematic. TLCL edges typically contain electrode layer contacts and require encapsulation. FIG. 19 illustrates the location of the integrated receiver coil of the drive signal coupler receiver element. It is understood that such a signal receiver element can also be used as a receiver element of a power coupler to recharge the power storage 1350 (shown dashed) of an integral ocular prosthesis or to retard its depletion. For example, an eye glasses frame (including pianos) or an eye patch can be employed in a similar fashion as illustrated in FIG. 18 to recharge the power store 1350 (battery or capacitor) either during operation or at night. Such eye glasses frame or eye patch includes an external transmit element (power emitter driver coil) for transmitting power.

Particularly for purposes of initial or subsequent re-programming the signal coupler receiver element provides a physical programming interface for the ocular lens device controller 1330, for example an antenna.

The power storage 1350 can include a battery or a capacitor. With respect to the power source, it would be appreciated that integral intraocular prostheses are limited to low power implementations. For example, a 5V battery or capacitor can be employed providing sufficient operational duration. For example, for a 3.0 mm accommodative clear aperture 360 implementation a TLCL would consume 0.035 mW while total power consumption, for both TLCL 1302 and electronics package 1300, is around 0.20 mW. A dual TLCL having a 4.5 mm accommodative clear aperture 360 would consume 0.157 mW with a total power consumption of about 1.35 mW. Lower power operation is possible as a tradeoff against other ocular prosthesis operational parameters. For example, from a convergence signal transmission and detection perspective, a sufficient $\Delta I/\Delta t$ can be provided by employing 2V source and 10 mA pulses of 0.1 µs, wherein coil resistance would be R=2V/0.01 A=200 Ω expending P=200*0.01^2=20 mW instantaneous power during each pulse.

Figure 17:
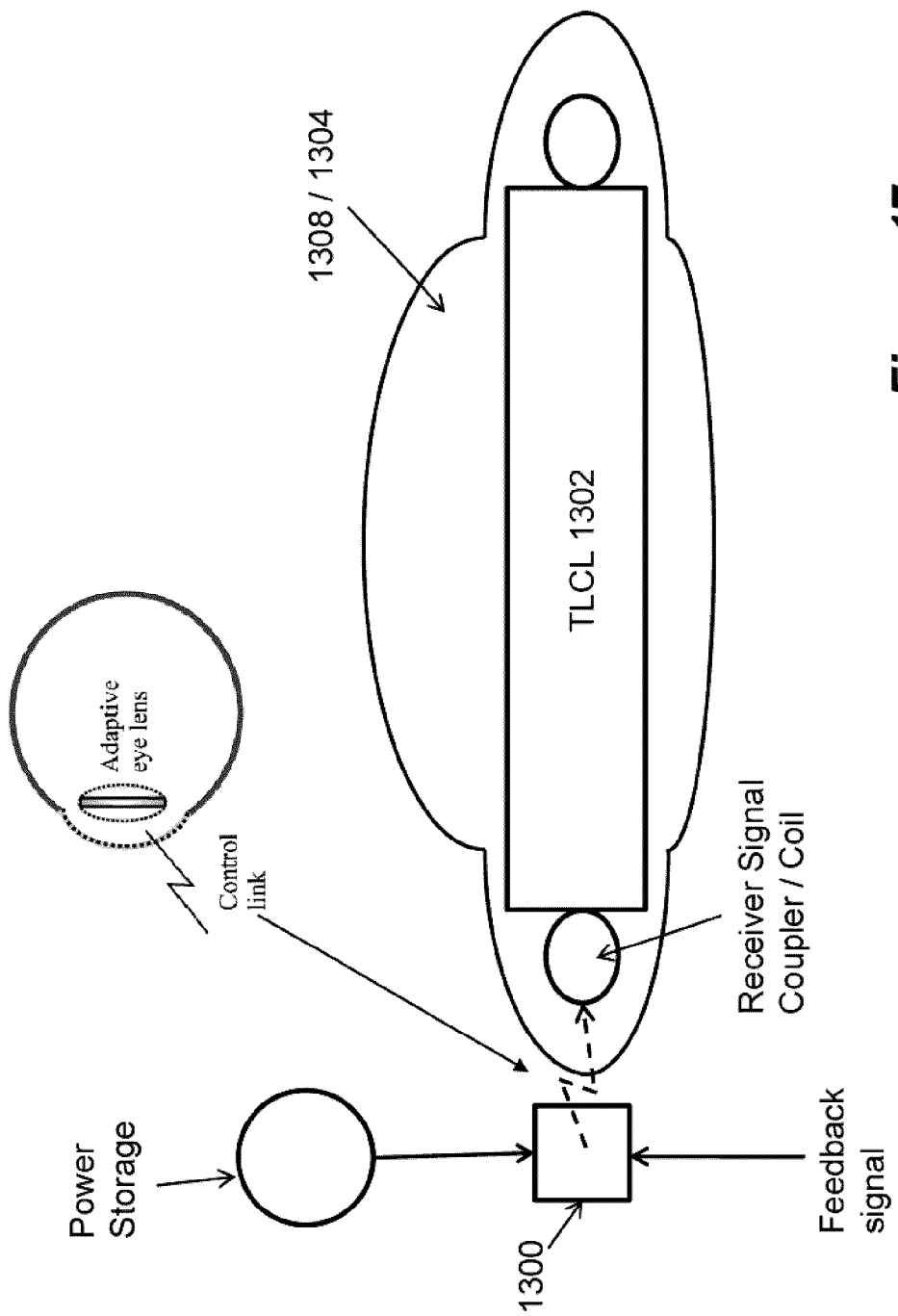
FIG. 17 is a schematic diagram illustrating an intraocular prosthesis having an external electronics package, the inset showing wireless control, in accordance with the proposed solution.

The invention is not limited to an integral intraocular prosthesis. FIG. 17 illustrates an intraocular prosthesis having integral TLCL 1302 and (receiver/signal coupler) coil, but an external electronics package 1300 and power source for example implemented in a glasses frame (including pianos).

The invention is not limited to the above description which assumes an aberration free eye, a perfectly manufactured intraocular prosthesis and on-optical axis placement of the ocular lens device. While some of the liquid crystal cells described above, and illustrated in the drawings, have a hole-patterned annular ring electrode, the invention is not limited thereto. For example, International PCT Application PCT/CA2010/002023 filed Dec. 23, 2010 entitled "Image Stabilization and Shifting in a Liquid Crystal Lens" claiming priority from Dec. 13, 2009, the entirety of which is incorporated herein by reference, describes tunable liquid crystal optical devices, including but not limited to lenses, having a segmented hole-patterned electrode for controlling the electric field across the liquid crystal layer enabling asymmetric phase profiles to be applied for light tilting, optical image stabilization and sub-pixel shift capability. With feedback from an image sensor, such geometry can be used for image stabilization. Co-pending, commonly assigned, U.S. Patent Application 2012/0113318 entitled "Methods of Adjustment Free Manufacture of Focus Free Camera Modules" claiming priority from 4 Nov. 2010, which is incorporated herein by reference, describes accounting for overall optical system optical error/aberration during TLCL manufacture.

While extensive reference has been made to an intraocular vision corrective prosthesis, the invention is not limited thereto, the above components and methods can be equally implemented in a contact lens.

The liquid crystal cells described above and illustrated in the drawings relate to lenses, but other optical devices can also be made using the proposed solution. For example, the liquid crystal material can be mixed with a material having a large anisotropy of absorption (otherwise called "dichroic absorbing" materials) to be controllably oriented to act as a polarization-independent shutter or as a diaphragm device. Differences in absorption coefficients between two orientation states (with respect to the polarization of light) can be orders of magnitude when the material properties, typically the molecule length (namely the aspect ratio) as well its ability to absorb light within the desired spectrum, are well suited. Carbon nanotubes, chains of dichroic dyes, metal or semiconductor nanorods can offer the aspect ratio, absorption properties and stability to be suitable for such applications.

While the invention has been shown and described with referenced to preferred embodiments thereof, it will be recognized by those skilled in the art that various changes in form and detail may be made therein without departing from the spirit and scope of the invention as defined by the appended claims.

What is claimed is:

1. An ocular lens prosthesis for correcting eye vision, the ocular lens prosthesis comprising:
   a tunable lens component for a first eye including:
      at least one coil; and
      a circuit connected to said coil, said circuit being configured to:
         detect an accommodation stimulus signal;
         communicate signals between said coil and a neighboring eye; and
         detect a variation in electromagnetic fields and correlate said variation with at least one of an orientation of said first or neighboring eye or a target object distance from said first or neighboring eye; and
         dynamically adjust an optical power of said lens based on at least one of the detected accommodation stimulus signal, the communicated signals, or the correlated variation.

2. A prosthesis as claimed in claim 1, wherein said circuit comprises a remote re-programmable controller.

3. A prosthesis as claimed in claim 2, wherein said reprogrammable controller is further configured to employ said coil for communications with an external programming module.

4. A prosthesis as claimed in claim 1, wherein a pair of said ocular lens prostheses forms a vision corrective system providing consorted dynamic adaptation, wherein said coil is configured to generate and emit an electromagnetic convergence signal during an even time period while an external electromagnetic convergence signal is detected by said coil during an odd time period.

5. A prosthesis as claimed in claim 4, wherein said emitted convergence signal comprises a carrier frequency, information being carried over to the other ocular lens prosthesis by modulating said carrier frequency, wherein communication between said prostheses provides for at least one of:
   said prosthesis relying on a stimulus signal detected by the other prosthesis and
   said prosthesis validating a detected stimulus signal detected by said prosthesis.

6. A prosthesis as claimed in claim 3, wherein detecting said ambient electromagnetic field variation from tissue associated with said eye to correlate with accommodation triggering in said eye, the circuit is configured to establish a calibration using one of: an external eye convergence measurement communicated to said prosthesis and validation of the stimulus detected by said prosthesis via communication between said prostheses, wherein communication between said prostheses includes one of direct inter-prostheses communication and communication via said external programming module.

7. A prosthesis as claimed in claim 1, said tunable lens comprising:
   a tunable liquid crystal lens;
   a tunable liquid crystal lens drive signal generator configured to generate at least one drive signal component to vary an optical power provided by said tunable liquid crystal lens;
   a tunable liquid crystal lens driver configured to control said drive signal generator to set at least one drive signal parameter to focus said prosthesis at a convergence distance in response to a stimulus signal; and
   a remote re-programmable tunable liquid crystal lens controller configured to perform one of:
      transmit said accommodation stimulus signal; and
      provide said driver a convergence stimulus signal from said coil.

8. An ocular lens prosthesis for correcting eye vision, the ocular lens prosthesis having a tunable lens component comprising:
   at least one coil;
   a circuit connected to said coil, said circuit being configured to detect an accommodation stimulus signal, to dynamically adjust an optical power of said lens and to perform one or more of: communicate signals between said coil and a corresponding coil of another ocular lens prosthesis associated with a neighboring eye, detect a variation in electromagnetic fields and correlate said variation to at least one of an orientation of said eye and a target object distance, or detect an ambient electromagnetic field variation from tissue associated with said eye to correlate with accommodation triggering in said eye;
   a tunable liquid crystal lens connected to said circuit;
   a tunable liquid crystal lens drive signal generator configured to generate at least one drive signal component to vary an optical power provided by said tunable liquid crystal lens;
   a tunable liquid crystal lens driver configured to control said drive signal generator to set at least one drive signal parameter to focus said prosthesis at a convergence distance in response to at least one of said accommodation stimulus signal or a convergence stimulus signal; and
   a remote re-programmable tunable liquid crystal lens controller configured to perform one of: transmit said accommodation stimulus signal, or provide said driver said convergence stimulus signal from said coil,
   wherein a normal axis of said coil is offset at an angle with respect to an optical axis of said tunable liquid crystal lens.

9. A prosthesis as claimed in claim 7, wherein said coil is configured to receive recharge power from an external power emitter coil, said prosthesis comprising a power store configured to store electrical power to drive said tunable liquid crystal lens, said generator, said driver and said controller.

10. A prosthesis as claimed in claim 7 comprising a substantially transparent encapsulating material, said encapsulating material being configured to provide a fixed optical power element for augmenting the optical power of said tunable liquid crystal lens.

11. A prosthesis as claimed in claim 10, said tunable liquid crystal lens having an accommodation clear aperture, said encapsulating material forms a lenticular shape at least over said accommodation clear aperture of the tunable liquid crystal lens, said encapsulating material encapsulating said generator, driver, controller, power storage and said coil component arranged about the periphery of said tunable liquid crystal lens.

12. A prosthesis as claimed in claim 1, wherein said vision prosthesis is an intraocular lens prosthesis for replacing a natural lens of an eye.

13. A prosthesis as claimed in claim 1, wherein said vision prosthesis is a contact lens.

14. A prosthesis as claimed in claim 1, wherein said circuit is configured to detect an accommodation stimulus signal by detecting a variation in an electromagnetic field and correlating said detected electromagnetic field variation to a relative orientation of said eyes corresponding to a viewing distance.

15. A prosthesis as claimed in claim 14, wherein said circuit is configured to:
generate pulses in said coil of one eye to generate a magnetic flux pulse detectable by said coil of the other eye, said pulses being generated with a frequency suitable to capture microsaccades motion;
measure using said coil a plurality of EMF values corresponding to said pulses from the coil of the other eye, said plurality of values being sufficient to capture microsaccades motion with the eyes fixed on an object at a viewing distance and orientation;
calculate an EMF average value from said plurality of EMF values;
obtain a EMF variation spread value from said plurality of EMF values; and
determine at least one of said viewing distance and said eye orientation from said EMF average value and said EMF variation spread value.

16. A prosthesis as claimed in claim 15, wherein said circuit comprises a high frequency band pass filter and a threshold trigger for detecting each of said pulse from the coil of the other eye.

17. A prosthesis as claimed in claim 14, wherein said circuit is configured to:
generate said accommodation signal having a frequency in said coil of one eye to generate a magnetic flux detectable by said coil of the other eye, said accommodation signal being generated with a frequency suitable to capture microsaccades motion;
measure using said coil a plurality of EMF values at a measurement frequency sufficient to capture microsaccades motion with the eyes fixed on an object at a viewing distance and orientation;
calculate an EMF average value from said plurality of EMF values;
obtain an EMF variation spread value from said plurality of EMF values; and
determine at least one of said viewing distance and said eye orientation from said EMF average value and said EMF variation spread value.

18. A prosthesis as claimed in claim 14, wherein said circuit comprises a phase locked loop amplifier for maintaining synchronization with the circuit of the other eye.

19. A prosthesis as claimed in claim 14, wherein said circuit of the other eye uses said coil to communicate a value of said viewing distance to said circuit of the one eye.

20. A prosthesis as claimed in claim 14, wherein said circuit generates pulses in said coil of approximately 1 to 20 nanoseconds, and preferably less than 5 nanoseconds in duration, and more preferably less than 2 nanoseconds.

21. The prosthesis of claim 8, wherein said circuit is configured to:
measure using said coil a plurality of EMF values sufficient to capture microsaccades motion with the eyes fixed on an object at a viewing distance and orientation;
calculate an EMF average value from said plurality of EMF values;
obtain an EMF variation spread value from said plurality of EMF values; and
determine at least one of said viewing distance and said eye orientation from said EMF average value and said EMF variation spread value.

22. The prosthesis of claim 1 wherein said neighboring eye comprises another ocular lens prosthesis having a corresponding coil.

23. The prosthesis of claim 1 wherein said circuit is configured to detect an ambient electromagnetic field variation from tissue associated with said first or neighboring eye to correlate with accommodation triggering in said first eye.

* * * * *